(12) United States Patent
Schlapfer et al.

(10) Patent No.: US 10,623,498 B2
(45) Date of Patent: *Apr. 14, 2020

(54) AUTOMATIC UPDATING OF CARE TEAM ASSIGNMENTS IN ELECTRONIC HEALTH RECORD SYSTEMS BASED ON DATA FROM VOICE COMMUNICATION SYSTEMS

(71) Applicant: Vocera Communications, Inc., San Jose, CA (US)

(72) Inventors: Martin Schlapfer, Gilroy, CA (US); David Shively, Fremont, CA (US)

(73) Assignee: Vocera Communications, Inc., San Jose, CA (US)

( * ) Notice: Subject to any disclaimer, the term of this patent is extended or adjusted under 35 U.S.C. 154(b) by 130 days.

This patent is subject to a terminal disclaimer.

(21) Appl. No.: 16/004,393

(22) Filed: Jun. 10, 2018

(65) Prior Publication Data

US 2018/0295186 A1 Oct. 11, 2018

Related U.S. Application Data

(63) Continuation of application No. 14/823,427, filed on Aug. 11, 2015, now Pat. No. 10,257,277.

(51) Int. Cl.
*H04L 29/08* (2006.01)
*G16H 40/20* (2018.01)
(Continued)

(52) U.S. Cl.
CPC ............ *H04L 67/12* (2013.01); *G16H 40/20* (2018.01); *H04L 67/02* (2013.01); *G06Q 50/24* (2013.01); *G16H 10/60* (2018.01)

(58) Field of Classification Search
CPC ......... H04L 67/12; H04L 67/02; G16H 40/20; G16H 10/60; G06Q 50/24
See application file for complete search history.

(56) References Cited

U.S. PATENT DOCUMENTS 6,892,083 B2   5/2005   Shostak
7,698,156 B2   4/2010   Martucci
(Continued)

OTHER PUBLICATIONS

International Search Report and Written Opinion for related International Application No. PCT/US2016/045112 dated Nov. 9, 2016.
(Continued)

*Primary Examiner* — Blake J Rubin
(74) *Attorney, Agent, or Firm* — The Marbury Law Group, PLLC

(57) ABSTRACT

Various embodiments enable updating care team assignments data in multiple systems of a hospital. Various embodiments may include receiving by a first server a first message including information corresponding to a hospital personnel assignment for a predetermined location within a hospital, determining, by the first server, whether a hospital personnel assignment data record corresponding to the predetermined location within the hospital reflects a current hospital personnel assignment for the predetermined location within the hospital based on whether the first message is received from a second server or a third server, and updating, by the first server, the hospital personnel assignment data record to include the information corresponding to the hospital personnel assignment for the predetermined location within the hospital included in the first message in response to determining that the hospital personnel assignment data record does not reflect the current hospital personnel assignment for the predetermined location.

21 Claims, 14 Drawing Sheets

(51) Int. Cl.
*G06Q 50/24* (2012.01)
*G16H 10/60* (2018.01)

(56) References Cited

U.S. PATENT DOCUMENTS

| | | | |
|---|---|---|---|
| 8,098,806 B2 | 1/2012 | Shostak | |
| 8,260,779 B2 | 9/2012 | Hudgins et al. | |
| D679,673 S | 4/2013 | Wheaton et al. | |
| 8,583,694 B2 | 11/2013 | Siegel et al. | |
| 8,661,453 B2 | 2/2014 | Mathur et al. | |
| 9,058,635 B1 | 6/2015 | Rybkin | |
| 10,489,023 B2* | 11/2019 | Robbins | G06F 3/0482 |
| 10,496,788 B2* | 12/2019 | Amarasingham | G06F 19/00 |
| 2004/0043797 A1 | 3/2004 | Shostak | |
| 2005/0143671 A1 | 6/2005 | Hastings et al. | |
| 2006/0053035 A1 | 3/2006 | Eisenberg | |
| 2006/0261962 A1* | 11/2006 | Berenguer | G08B 21/0423 340/573.1 |
| 2006/0290519 A1 | 12/2006 | Boate et al. | |
| 2007/0033073 A1* | 2/2007 | Tajaliawal | G06Q 50/22 705/3 |
| 2007/0174079 A1 | 7/2007 | Kraus | |
| 2007/0185736 A1 | 8/2007 | Cervi et al. | |
| 2008/0021733 A1* | 1/2008 | Nagaeda | G16H 40/20 705/2 |
| 2008/0046292 A1 | 2/2008 | Myers et al. | |
| 2008/0106374 A1 | 5/2008 | Sharbaugh | |
| 2008/0221396 A1 | 9/2008 | Garces et al. | |
| 2009/0089100 A1 | 4/2009 | Nenov et al. | |
| 2009/0099862 A1* | 4/2009 | Fireman | G06F 19/3418 705/2 |
| 2009/0132276 A1 | 5/2009 | Petera | |
| 2009/0143045 A1 | 6/2009 | Graves et al. | |
| 2010/0017231 A1 | 1/2010 | Galbraith et al. | |
| 2010/0286997 A1 | 11/2010 | Srinivasan | |
| 2011/0071850 A1* | 3/2011 | Nuthi | G06Q 50/22 705/3 |
| 2011/0106561 A1 | 5/2011 | Eaton, Jr. et al. | |
| 2011/0137680 A1 | 6/2011 | Sweeney | |
| 2011/0166884 A1 | 7/2011 | Lesselroth et al. | |
| 2012/0078660 A1 | 3/2012 | Mangicaro et al. | |
| 2012/0278101 A1 | 11/2012 | Homchowdhury et al. | |
| 2012/0278104 A1 | 11/2012 | Traughber et al. | |
| 2012/0290322 A1 | 11/2012 | Bergman et al. | |
| 2013/0024213 A1* | 1/2013 | Poon | A61B 5/0002 705/3 |
| 2013/0085771 A1 | 4/2013 | Ghanbari et al. | |
| 2013/0110547 A1 | 5/2013 | Englund et al. | |
| 2013/0124523 A1 | 5/2013 | Rogers et al. | |
| 2013/0285947 A1 | 10/2013 | Hunter et al. | |
| 2014/0006943 A1 | 1/2014 | Robbins et al. | |
| 2014/0249854 A1 | 9/2014 | Moore et al. | |
| 2014/0365242 A1 | 12/2014 | Neff | |
| 2014/0379357 A1 | 12/2014 | Srivathsa et al. | |
| 2015/0081332 A1* | 3/2015 | Casper | G16H 10/60 705/3 |
| 2015/0254412 A1 | 9/2015 | Humphrys et al. | |
| 2015/0288682 A1 | 10/2015 | Bisroev et al. | |
| 2015/0288797 A1 | 10/2015 | Vincent | |
| 2015/0294086 A1* | 10/2015 | Kare | G06F 19/3481 705/3 |
| 2015/0302539 A1 | 10/2015 | Mazar et al. | |
| 2016/0012196 A1 | 1/2016 | Mark et al. | |
| 2016/0026837 A1 | 1/2016 | Good et al. | |
| 2016/0063189 A1 | 3/2016 | Soon-Shiong et al. | |
| 2016/0210429 A1 | 7/2016 | Ortiz et al. | |
| 2016/0321404 A1 | 11/2016 | Ginsburg | |
| 2017/0048323 A1 | 2/2017 | Schlaper et al. | |
| 2017/0147756 A1 | 5/2017 | Moharir | |
| 2019/0080796 A1* | 3/2019 | Greiner | G16H 30/20 |

OTHER PUBLICATIONS

International Search Report and Written Opinion for related International Application No. PCT/US2016/045112 dated Nov. 9, 2016, 11 pages.

Transmittal of International Preliminary Report on Patentability from the International Bureau for International Patent Application No. PCT/US2016/045112, dated Feb. 22, 2018, 8 pages.

* cited by examiner

FIG. 2A

| 202 | |
|---|---|
| Location ID | Room 1 |
| Nurse ID | Nancy |
| Assistant ID | Allen |
| Primary Doctor ID | - |
| Specialist Doctor ID | - |
| Hospitalist ID | Hugh |
| Patient ID | - |

Incoming Accurate Shift-based and Location-based information From voice communications server

FIG. 2B

| 252 | |
|---|---|
| Location ID | Room 1 |
| Patient ID | Patty |
| Nurse ID | Nancy, Nigel, Nina |
| Assistant ID | - |
| Primary Doctor ID | Tom |
| Specialist Doctor ID | Sam |
| Hospitalist ID | Harry |

Incoming Accurate Patient and Physician information From EHR server

FIG. 3A

| | 302 |
|---|---|
| Location ID | Room 1 |
| Nurse ID | Nancy |
| Assistant ID | Allen |
| Primary Doctor ID | Tom |
| Specialist Doctor ID | Sam |
| Hospitalist ID | Harry |
| Patient ID | Patty |

310 — 302
312 — Location ID
314 — Nurse ID
316 — Assistant ID
318 — Primary Doctor ID
320 — Specialist Doctor ID
322 — Hospitalist ID / Patient ID Outgoing Synchronized Data to voice communications server

FIG. 3B

| | 352 |
|---|---|
| Location ID | Room 1 |
| Patient ID | Patty |
| Nurse ID | Nancy |
| Assistant ID | Allen |
| Primary Doctor ID | Tom |
| Specialist Doctor ID | Sam |
| Hospitalist ID | Harry |

360 — 352
362 — Location ID
364 — Patient ID
366 — Nurse ID
368 — Assistant ID
370 — Primary Doctor ID
372 — Specialist Doctor ID / Hospitalist ID Outgoing Synchronized Data to EHR server

799

```
<normalizer>
    <entry>
        <format>$1 Room $2 : Hospital A</format>
        <node>
            <input>/PV1-3-1</input>
            <pattern>SJ ([0-9]+ North).*</pattern>
            <variables>$*,$1</variables>
            <node>
                <input>/PV1-3-2</input>
                <pattern>^.*([0-9]{2})$</pattern>
                <variables>$*,$2</variables>
                <node>
                    <input>$2</input>
                    <pattern>0*([0-9]+)</pattern>
                    <variables>$*,$2</variables>
                </node>
            </node>
        </node>
        <node>
            <input>/PV1-3-1</input>
            <pattern>SJ (ICU).*</pattern>
            <variables>$*,$1</variables>
            <node>
                <input>/PV1-3-2</input>
                <pattern>CC([0-9]+)</pattern>
                <variables>$*,$2</variables>
                <node>
                    <input>$2</input>
                    <pattern>0*([0-9]+)</pattern>
                    <variables>$*,$2</variables>
                </node>
            </node>
        </node>
    </entry>
</normalizer>
```

FIG. 7C

AUTOMATIC UPDATING OF CARE TEAM ASSIGNMENTS IN ELECTRONIC HEALTH RECORD SYSTEMS BASED ON DATA FROM VOICE COMMUNICATION SYSTEMS

RELATED APPLICATIONS

This application is a continuation of U.S. patent application Ser. No. 14/823,427 entitled "Automatic Updating of Care Team Assignments in Electronic Health Record Systems Based on Data from Voice Communication Systems" filed Aug. 11, 2015, the entire contents of which are hereby incorporated by reference for all purposes.

BACKGROUND

Hospitals may define assignments of doctors, nurses, and other staff to patients, shifts, and locations within the hospitals (referred to as "care team assignments"). Typically, these care team assignments are recorded and tracked using an electronic hospital record (EHR) system. Care team assignments may change over time, such as due to shift changes, worker absences, discharges, and other events within a hospital, and so EHR systems can become out-of-date or otherwise include inaccurate information regarding current care team assignments. One reason for inaccurate care team assignments data may be due to the required interactions of care team members with the EHR system. For example, in order to update a care team assignment with an EHR system, a nurse may need to manually log into a terminal and indicate whether she or other professionals have completed a shift, showed up for work, and otherwise are or are not currently associated with a care team assignment. With unreliable care team assignments stored in the EHR systems, there may be a reduced ability for hospital staff to identify, communicate with, and/or schedule care team workers to provide care to patients and rooms within the hospital. For example, with unreliable care team assignment data in EHR systems, physicians may be left out of workflows for patients, team members may become frustrated, and other communication systems may be marginalized due to the inaccurate data of the care team assignments.

SUMMARY

Various embodiments provide methods, devices, systems, and non-transitory process-readable storage media for automatically updating care team assignments data in multiple systems associated with a hospital (e.g., such as but not limited to an electronic health record (EHR) systems and a voice communication system). Various embodiments may include receiving by a first server a first message including information corresponding to a hospital personnel assignment for a predetermined location within a hospital, determining, by the first server, whether a hospital personnel assignment data record corresponding to the predetermined location within the hospital reflects a current hospital personnel assignment for the predetermined location within the hospital based on whether the first message is received from a second server or a third server, and updating, by the first server, the hospital personnel assignment data record to include the information corresponding to the hospital personnel assignment for the predetermined location within the hospital included in the first message in response to determining that the hospital personnel assignment data record does not reflect the current hospital personnel assignment for the predetermined location.

Some embodiments may further include obtaining, by the first server, the hospital personnel assignment data record based on the predetermined location within the hospital in response to receiving the first message in which the hospital personnel assignment data record may include a first data field associated with the predetermined location, a second data field associated with information assumed to be accurate when provided by the second server, and a third data field associated with information assumed to be accurate when provided by the third server. In such embodiments, determining whether the hospital personnel assignment data record corresponding to the predetermined location within the hospital reflects the current hospital personnel assignment for the predetermined location within the hospital comparing, by the first server, the information corresponding to the hospital personnel assignment for the predetermined location within the hospital included in the first message to the second data field in response to determining that the first message is received from the third server, determining, by the first server, that the hospital personnel assignment data record does not reflect the current hospital personnel assignment for the predetermined location within the hospital in response to determining that the second data field is empty or the information within the second data field does not match the information corresponding to the hospital personnel assignment for the predetermined location within the hospital included in the first message, and determining, by the first server, that the hospital personnel assignment data record reflects the current hospital personnel assignment for the predetermined location within the hospital in response to determining that information within the second data field includes the information corresponding to the hospital personnel assignment for the predetermined location within the hospital included in the first message. Alternatively in such embodiments, determining whether the hospital personnel assignment data record corresponding to the predetermined location within the hospital reflects the current hospital personnel assignment for the predetermined location within the hospital may include comparing, by the first server, the information corresponding to the hospital personnel assignment for the predetermined location within the hospital included in the first message to the second data field in response to determining that the first message is received from the third server, determining, by the first server, that the hospital personnel assignment data record does not reflect the current hospital personnel assignment for the predetermined location within the hospital in response to determining that the second data field is empty or the information within the second data field does not match the information corresponding to the hospital personnel assignment for the predetermined location within the hospital included in the first message, and determining, by the first server, that the hospital personnel assignment data record reflects the current hospital personnel assignment for the predetermined location within the hospital in response to determining that information within the second data field includes the information corresponding to the hospital personnel assignment for the predetermined location within the hospital included in the first message. Alternatively in such embodiments, determining whether the hospital personnel assignment data record corresponding to the predetermined location within the hospital reflects the current hospital personnel assignment for the predetermined location within the hospital may include comparing, by the first server, the information corresponding to the hospital personnel assignment for the predetermined location within the hospital included in the first message to the third data field in response to determining that the first message is received from the second server, determining, by the first server, that the hospital personnel assignment data record does not reflect the current hospital personnel assignment for the predetermined location within the hospital in response to determining that the third data field is empty or the information within the third data field does not match the information corresponding to the hospital personnel assignment for the predetermined location within the hospital included in the first message, and determining, by the first server, that the hospital personnel assignment data record reflects the current hospital personnel assignment for the predetermined location within the hospital in response to determining that information within the third data field includes the information corresponding to the hospital personnel assignment for the predetermined location within the hospital included in the first message.

Some embodiments may further include transmitting, by the first server, a second message to the second server in response to determining that the first message is received from the third server and the hospital personnel assignment data record corresponding to the predetermined location within the hospital does not reflect the current hospital personnel assignment for the predetermined location within the hospital, and transmitting, by the first server, a third message to the third server in response to determining that the first message is received from the second server and the hospital personnel assignment data record corresponding to the predetermined location within the hospital does not reflect the current hospital personnel assignment for the predetermined location within the hospital. In some embodiments, the subscription may be to receive asynchronous notifications via an HTTP connection from the first server.

In some embodiments, the second server may be a voice communications server, and the third server may be an EHR server. In some embodiments, the first message may indicate a change in the hospital personnel assignment for the predetermined location within the hospital.

Further embodiments include a computing device configured with processor-executable instructions for performing operations of the methods summarized above. Further embodiments include a non-transitory processor-readable medium on which is stored processor-executable instructions configured to cause a computing device to perform operations of the methods summarized above. Further embodiments include a communication system including a computing device configured with processor-executable instructions to perform operations of the methods summarized above.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

FIG. 2A is a component block diagram that illustrates an exemplary data structure including data from a voice communications server that may be received by an embodiment sync server.

FIG. 2B is a component block diagram that illustrates an exemplary data structure including data from an electronic hospital record server that may be received by an embodiment sync server.

FIG. 3A is a component block diagram that illustrates an exemplary data structure including synced data that may be transmitted by a sync server to a voice communications server according to various embodiments.

FIG. 3B is a component block diagram that illustrates an exemplary data structure including synced data that may be transmitted by a sync server to an electronic hospital record server according to various embodiments.

FIG. 7C is a diagram of an exemplary code for normalizing HL7 message data received by a sync server.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various embodiments provide methods and systems for updating care team assignments data in multiple systems associated with a hospital by leveraging information stored within a communication system database. In some typical scenarios, hospital EHR systems may become out of date when staff fail to update their status, however it has been observed that the status information in a hospital communication system database may be more reliable due to the check-in/check-out procedures for hospital communicators. In view of this, in some embodiments a sync server may compare staff assignments to data stored in the EHR system to staff assignments to communicators stored in the hospital communication system database, and update the EHR system database as appropriate. Various embodiments include translating and correlating different database fields and values in order to affect such comparisons and updates when the two databases use inconsistent data structures, terminology, and organizations.

The word "exemplary" is used herein to mean "serving as an example, instance, or illustration." Any implementation described herein as "exemplary" is not necessarily to be construed as preferred or advantageous over other implementations.

The term "computing device" is used herein to refer to an electronic device equipped with at least a processor. Examples of computing devices may include mobile devices (e.g., cellular telephones, wearable devices, smart-phones, web-pads, tablet computers, Internet enabled cellular telephones, Wi-Fi® enabled electronic devices, personal data assistants (PDA's), laptop computers, etc.), personal computers, and server computing devices. In various embodiments, computing devices may be configured with memory or storage as well as networking capabilities, such as network transceiver(s) and antenna(s) configured to establish a wide area network (WAN) connection (e.g., a cellular network connection, etc.) and/or a local area network (LAN) connection (e.g., a wired/wireless connection to the Internet via a Wi-Fi® router, etc.). Computing devices may also include voice communications badge devices, examples of which are illustrated below with reference to FIGS. 1 and 8.

Figure 9:
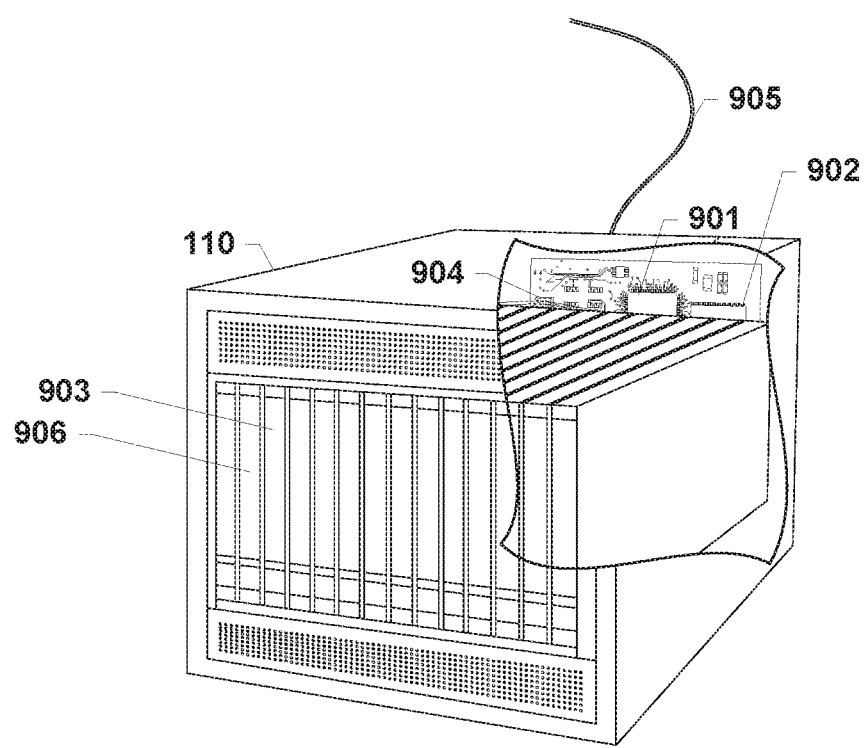
FIG. 9 is a component block diagram of a server computing device suitable for use in some embodiments.

The term "server" (or "server computing device") is used to refer to any computing device capable of functioning as a server, such as a master exchange server, web server, mail server, document server, and a personal or mobile computing device configured with software to execute server functions. A server may be a dedicated computing device or a computing device including a server module (e.g., running an application which may cause the computing device to operate as a server). An exemplary server is described below with reference to FIG. 9.

For the purposes of this disclosure, various embodiments may involve different servers, including at least "EHR servers" that are servers configured to maintain and provide data linked to patients admitted (or discharged) from a hospital, "voice communications servers" that are servers configured to maintain and provide data that is based on communications received from wireless voice communications badge devices used by hospital personnel, and "sync servers" that are servers configured to synchronize data that is received from both EHR servers and voice communications servers.

The term "HL7 message" is used herein to refer to messages that utilize the Health Level 7 (HL7) set of international standards for the transfer of clinical and administrative data between hospital information systems. HL7 messages typically include various data fields related to patient data, such as data fields indicating a point-of-care (e.g., PV1-3-1), a room for a patient (e.g., PV1-3-2), a bed associated with the patient (e.g., PV1-3-3), the facility the patient is in (e.g., PV1-3-4), etc. For the purposes of this disclosure, EHR servers may utilize HL7 messages to provide or receive data. The term "Admit, Discharge, Transfer (ADT) message" is used herein to refer to a type of HL7 message that may be processed by a computing device. There may be various configurations of ADT messages based on the context under which the ADT messages are transmitted or received (e.g., in response to particular trigger events, etc.). For example, a first type of ADT message may be an update message and a second type of ADT message may be an admit message. In various embodiments, a sync server may be configured to exchange HL7 messages (e.g., ADT messages) with an EHR server.

The term "care team" is used herein to refer to the hospital personnel (e.g., nurses, nurse assistants, doctors, specialists, hospitalists, etc.) assigned to provide various services for inpatient location(s) within the hospital. For example, a care team may include the nurses currently assigned to care for patients within certain wing(s), room(s), bed(s), or floor(s) of the hospital. The term "care team assignment" is used herein to refer to assignments or associations of hospital personnel with relation to time period(s)/shift(s) (e.g., night shift, day shift, etc.), patient(s), and/or location(s) within the hospital. The term "care team assignment data" is used herein to refer to data (or data record(s)) that associates identifiers, codes, and/or other information corresponding to the hospital personnel, shift(s), patient(s), and/or location(s) of a care team assignment. Exemplary illustrations of data records or structures that include care team assignment data are shown below in FIGS. 2A-3B.

Some care team assignments may be location-based and/or shift-based. For example, care team members may be assigned by their role (e.g., nurse, nurse assistant, general practitioner, cardiologist, hospitalist, etc.) to an inpatient location in a hospital (e.g., Room 101, Emergency Room, etc.) for a specific shift (e.g., night shift, morning shift, etc.). Location-based care team assignments may be associated with any combination of room(s), bed(s), set(s) of beds, building(s), and/or hospital unit(s). For example, a first nurse assistant may be assigned to Bed #5 in Room #123 of Building D at the hospital. As another example, a general physician may be assigned to a pod of beds labeled "Pod A". As another example, a registered nurse may be assigned to "Unit 4" in a children's wing of the hospital. Location-based and/or shift-based care team assignments may or may not explicitly indicate any associated patients. For example, location-based and/or shift-based care team assignment data may indicate a room number, a nurse, and shift identifiers but not any patient name or identifier. For the purposes of this disclosure, such location-based and/or shift-based care team assignment data may typically originate from a voice communications server. In other words, the voice communications server may typically be considered the "source of truth" (or source of accurate, up-to-date data) for location-based and/or shift-based care team assignment data. However, in some cases, accurate location-based and/or shift-based care team assignment data may be provided by other servers, such as an EHR server. The voice communications server may be configured to update care team assignments data in response to voice communications received via voice communications badge devices carried by hospital personnel, a mobile application running on a mobile device (e.g., a doctor or nurse's smartphone, etc.), and/or a website or web-based client accessed by various care team members and/or hospital personnel. Further, location-based and/or shift-based care team assignment data may be assumed to include accurate information for at least the care team members (e.g., nurses, nurse assistants, etc.) assigned to a particular location in the hospital at a given time/shift.

Some care team assignments may be patient-based, and related care team assignments data may primarily indicate physician associations with specific patients located in specific locations of the hospital. For example, patient-based care team assignment data may indicate that a particular patient "B" in Room #123 is associated with a particular general physician "T" and a cardiologist "C". Typically, patient-based care team assignment data indicates long-term relationships that persist as the patient moves through different locations and/or shifts at the hospital. For example, the general physician indicated in patient-based care team assignment data may not change as the patient stays in the hospital over multiple shifts (e.g., from morning to night time). Patient-based care team assignments may or may not explicitly indicate location-based and/or shift-based information, such as nurses assigned to a patient's room during a current shift. For example, patient-based care team assignment data may indicate a patient name, a room number for a certain room, and a general practitioner but not any attending nurse assigned to care for patients within the certain room. For the purposes of this disclosure, such patient-based care team assignment data may typically originate from an EHR server. In other words, the EHR server may typically be considered the "source of truth" (or source of accurate, up-to-date data) for patient-based care team assignment data. However, in some cases, accurate patient-based care team assignment data may be provided by other servers, such as a voice communications server as described herein. Patient-based care team assignment data may be assumed to include accurate information for at least a patient's identity, the patient's current location in the hospital, and the long-term care team members that are not associated with the patient based on a shift or location (e.g., the patient's general/family practitioner, the patient's cardiologist, etc.).

Multiple systems may be used to define and track care team assignments within a hospital. Typically, an EHR system may include a server configured to manage and distribute patient-based data, such as by transmitting HL7 data feeds that report associated physician(s) and assigned room(s)/bed(s) for all admitted patients.

Hospitals may employ a communications-based system to facilitate communications among hospital staff. In particular, the hospital may utilize communication devices, server(s), and software that enable care team members to wear voice communications badge devices or use other computing devices (e.g., mobile devices with apps, web clients, etc.) that enable such communications. Exemplary voice communication systems include wireless communication systems by Vocera Communications Inc., such as the systems described in commonly-held U.S. Pat. No. 6,892,083, the contents of which are hereby incorporated by reference in its entirety. In order to enable communications with the correct individual for a particular situation, such voice communication systems may maintain a database that matches communication devices to particular individuals and keeps track of their care team assignments and locations. For example, such wireless communication systems may accurately track the schedule, role, location, and availability of all on-duty nurses via real-time interactions with voice communication badge devices worn on lanyards or clipped to the nurses' uniforms.

Conventional, concurrently-employed systems may each store different data for various care team assignments for the hospital. For example, the EHR system may store data indicating that no nurse is assigned to a patient in Room #123, while the voice communication system may store data indicating that Nurse A is currently assigned to Room #123 in the hospital. With missing, incomplete, and/or inaccurate data potentially represented in either system, the hospital may encounter significant scheduling problems in managing and tracking care teams. For example, physicians who regularly need to contact nurses to coordinate patient care may check the EHR system to find multiple nurses inaccurately listed for a patient, causing the physicians to resort to other means of tracking down the right nurse (e.g., paging for unknown personnel over a hospital intercom, etc.). Further, users of tracking systems may not be able to properly use multiple systems simultaneously. A solution is needed that propagates the accurate care team assignment data from multiple systems.

The various embodiments provide methods, devices, systems, and non-transitory process-readable storage media for providing accurate, reliable care team assignment data for a hospital. In general, a sync server may be configured to detect and automatically update out-of-date care team assignment data that is reported and maintained by a first server associated with the hospital's voice communications system (i.e., the voice communications server) and a second server associated with the hospital's EHR system (i.e., the EHR server). The sync server may utilize existing APIs to register with each of the EHR server and voice communications server such that any changes to either corresponding system may be reported to the sync server. For example, in response to a nurse logging out of his shift via the voice communications system, the sync server may receive an event message indicating a change to his care team assignment, or may notice the change in care team assignment in a periodic review of the database. As another example, in response to a patient being admitted to the hospital, the sync server may receive an HL7 event message from the EHR system indicating the patient's identifier, primary care physician, and assigned room/bed in the hospital. Due to the nature and functioning of the voice communications system, as well as the way nurses and doctors relate to personal voice communication badge devices, the voice communications server may typically maintain accurate care team assignment data records and thus may transmit event messages that are accurate for location-based and/or shift-based care team assignment data. For example, event messages from the voice communications server may provide accurate data regarding the adding or removing of staff members from care teams. Event messages from the EHR server may be assumed to be generally accurate for patient-based data. For example, event messages from the EHR server may provide accurate data regarding changes to the patient's status (e.g., admission, discharge, etc.) and/or to the patient's long-term team of care providers (e.g., general physician, specialist, etc.). In some embodiments, the sync server may periodically poll the voice communications server for staff-to-location (e.g., room) care team assignments data.

In response to receiving an event message from the voice communications server or the EHR server, the sync server may intelligently process the event message to generate a common term database of information related to care team assignments (if necessary), and compare care team assignment data from both servers to find inconsistencies, errors, missing data, or out-of-date content for either. In some embodiments, intelligent heuristics may be used to identify inconsistencies indicative of outdated EHR server or voice communications server records. When accurate care team assignment data from one server is not represented in the data associated with the other server, the sync server may transmit update messages to correct and/or supplement care team assignment data stored on the other server, thus synchronizing care team assignment information stored in the two systems. In this manner, the sync server may bring together multiple data sources to ensure more complete and accurate data is represented in both the datasets of the EHR server and the voice communications server. With such reliable, synced data, hospital personnel may potentially use either system to easily identify and communicate with current care team members, improving both efficiency for workers and care for patients.

In various embodiments, the sync server may utilize several data processing operations and components to automate the synchronization process, which may require additional server and database storage components to be added to a conventional hospital network system. The data processing operations performed by the sync server may include receiving HL7 data streams from the EHR server and receiving group information from the voice communications server via an HTTP connection, identifying data fields from the received data that are related to care team assignments of the hospital, translating the identified data fields into common terms that are can be compared to care team assignment data from the either server (e.g., the EHR server and/or the voice communications server) using an intelligent translator (or normalization operations), forming a database of the common terms, using a heuristic or intelligence comparison algorithm to compare care team assignment data stored in the common terms database to identify incorrect or out-of-date records, and sending corrective data or messages.

In some embodiments, the voice communications server may add new data records (or instances) when a provider is logging into a care team for the first time. In some embodiments, the voice communications server may add new data records (or instances) when a provider is logging into a care team after a first time, in which case the new instances overwrite or otherwise replace any previous instances so that the older instances are no longer reported to other systems (e.g., EHR system via HL7 message, etc.).

In some embodiments, synced care team assignment data may be validated with a system configured to process ADT messages, such as a software application used by healthcare facilities to track patient census, patient care team, and patient admissions, discharges and transfers. For example, such a system may provide an HL7 2.3 data feed, including a "role" data field (i.e., a ROL segment), to indicate updated care team assignment data based on embodiment operations being performed by the sync server.

In some embodiments, multiple data sources may be connected to the sync server for the purposes of synchronizing stored care team assignment data. For example, in addition to receiving and analyzing data from the voice communications server and/or the EHR server, the sync server may receive care assignment data records from various other data sources, devices, servers, etc. that are configured to communicate with the sync server via supported messaging (e.g., HL7 messages via TCP connections, via programmatic interface connections such as a Vocera Administration Interface (VAI)) over HTTP connections, etc.), determine the most accurate assignments for each patient/room based on any or all the received data records, and transmit all necessary update messages to the various data sources (including the EHR server and/or the voice communications server) to ensure the more current, up-to-date care team assignment information is stored on the various data sources. In other words, the embodiment sync server may be configured to process and synchronize care team assignment data from a plurality of sources associated with a tracked facility (e.g., a hospital).

The embodiment techniques may be useful in several use cases, some examples of which include removing a provider (e.g., a nurse, nurse assistant, etc.) from active care team assignment data, adding a provider to active care team assignment data that has never been on the care team before, and adding a provider to active care team assignment data that has been on the care team before.

The following is an illustration of an embodiment process for removing a provider from an active care team assignment. At the end of her shift, a nurse may use a voice communications badge device to log-off of her care team assignment associated with a room and a bed group within a hospital. The voice communications badge device may transmit a message to the voice communications server that in turn updates the appropriate care team assignment data, indicating the nurse is logged off. The voice communications server may then transmit an event message to the sync server indicating the nurse is logged off of her care team assignment to the room and the bed group within the hospital. The sync server may then transmit an HL7 update message to the EHR server, indicating the change to the care team assignment now that the nurse logged-off. Such an update message may indicate all nurses for the hospital and include data indicating that the nurse has an "end time" set corresponding to the time she logged-off. In response, the sync server may receive from the EHR server an event message reflecting that the nurse is now indicated within the EHR server's records as being logged off of the care team assignment for the room and bed group.

Figure 1:
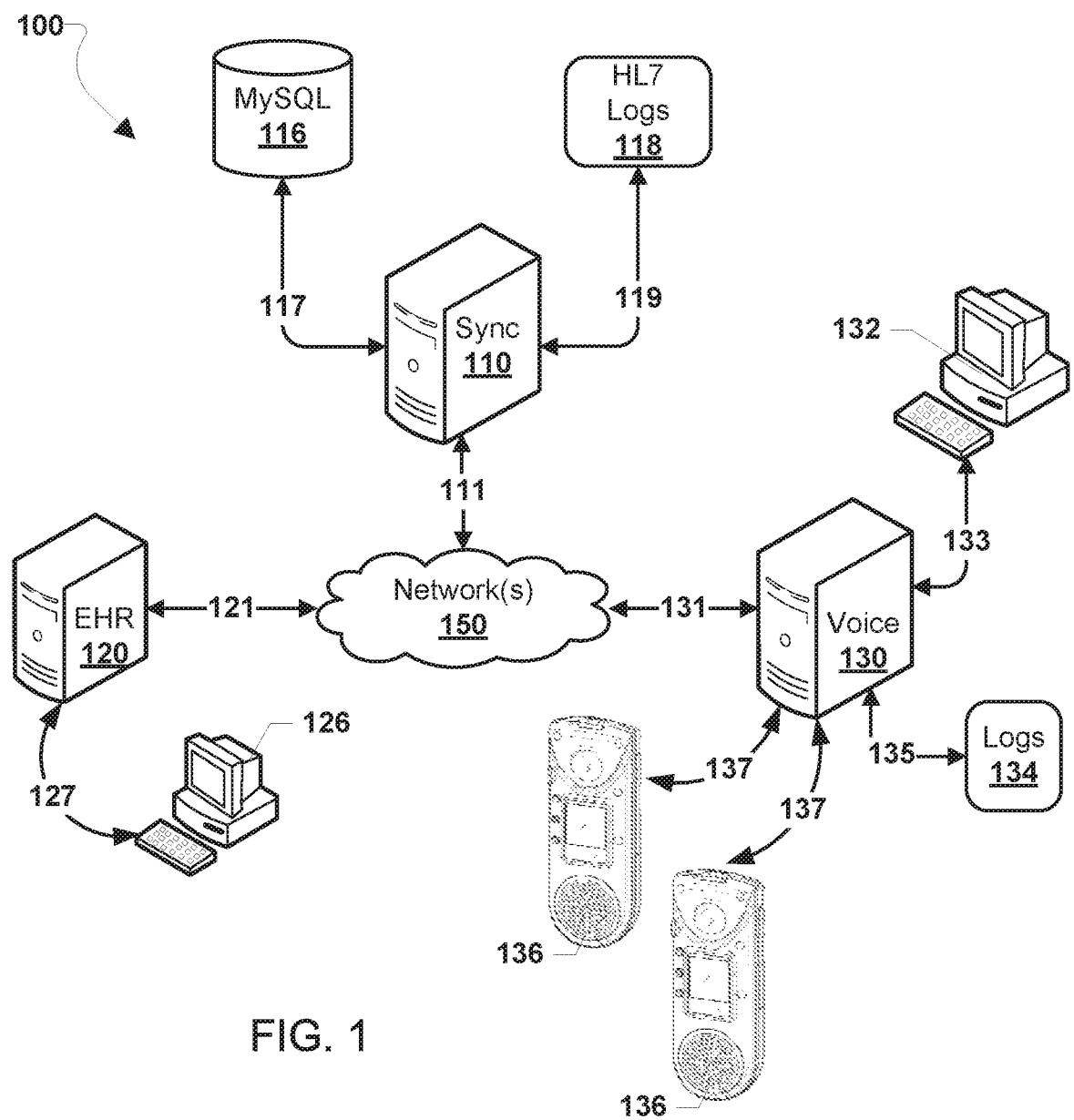
FIG. 1 is a component block diagram of a communication system including a sync server, an electronic hospital record server ("EHR"), and a voice communications server suitable for use in various embodiments.

FIG. 1 illustrates a communication system 100 including a sync server 110, an electronic hospital record server 120 ("EHR"), and a voice communications server 130 suitable for use with the various embodiments. Each of the servers 110, 120, 130 may be connected via one or more network(s) 150, such as a wide area network (WAN) (e.g., a cellular network, the Internet, etc.) and/or a local area network (LAN), such as a Wi-Fi® network associated with a hospital. For example, the EHR server 120 may utilize a wired or wireless connection 121 to the network 150, the sync server 110 may utilize a wired or wireless connection 111 to the network 150, and the voice communications server 130 may utilize a wired or wireless connection 131 to the network(s) 150. With such connections 121, 111, 131 to the network(s) 150, the servers 110, 120, 130 may exchange various messages between one another. For example, the sync server 110 may exchange messages with the voice communications server 130 via an HTTP connection over the network 150. As another example, the sync server 110 may exchange HL7 messages with the EHR server 120 via a TCP connection.

The EHR server 120 may be one or more server computing devices configured to at least transmit HL7 messages. In particular, the EHR server 120 may store, update, and transmit at least patient-based data, such as identifiers or codes indicating not only the identity of a patient admitted to a hospital, but also data indicating the physician, specialist, hospitalist, room, bed, wing, building, and/or status of the patient (e.g., discharged, admitted, etc.). The EHR server 120 may transmit HL7 messages including such patient-based data via one or more unidirectional data feeds, broadcasts, or multicasts. Transmission of the HL7 messages may be triggered on the occurrence of various events that change the patient-based data at the EHR server 120. For example, the EHR server 120 may transmit an HL7 message that indicates a patient identifier and a room identifier in response to the patient corresponding to the patient identifier being admitted to the hospital and being assigned to a room corresponding to the room identifier.

The EHR server 120 may receive information that is transmitted from various input sources, such as hospital administrator computers 126 connected to the EHR server 120 via wired or wireless connections 127. For example, the EHR server 120 may receive admitting and discharge reports in response to a nurse or administrator of the hospital entering data into a hospital terminal linked to or otherwise performing software associated with an EHR system. In some embodiments, the connection 127 between the EHR server 120 and the computers 126 may be via the network(s) 150. In some embodiments, the EHR server 120 may be connected to or otherwise may utilize a system capable of sending and receiving HL7 version 2.3 messages (e.g., ADT messages), such as messages that include a role (or "ROL") segment that indicates care team assignment information. For example, the EHR server 120 may be configured to send data feeds to an EHR interface engine that may be running ADT message-handling software or otherwise included within the sync server 110.

The voice communications server 130 may be one or more server computing devices configured to at least manage and distribute care team assignment data for a hospital. In particular, the voice communications server 130 may store, update, and transmit at least shift-based and/or location-based data of the various care team assignments of the hospital. In general, the voice communications server may transmit event messages that indicate changes or updates to care team assignments (or group information). Typically, changes to the care team assignments may be reported to the voice communications server 130 via a plurality of voice communications badge devices 136 connected to the voice communications server 130 via wired or wireless connections 137. For example, the voice communications server 130 may receive messages from any of the plurality of voice communications badge devices 136 that indicate users of the devices 136 (e.g., nurses, etc.) have logged-out of or logged-into a shift of working in a care team at the hospital. In some embodiments, the voice communications server 130 may receive messages from other devices used by care team members, such as mobile devices and/or computing devices executing web clients/browsers (not shown).

The voice communications server 130 may also be connected to a log module 134, such as a local database configured to store information related to communications from the various voice communications badge devices 136. For example, via the wired or wireless connection 135, the voice communications server 130 may transmit to the log module 134 data describing incoming messages from a nurse's voice communications badge device 136, the time of receipt, and any other location-based and/or shift-based information. In some embodiments, the log module 134 may be configured to simply read/write to a log without using a database. The voice communications server 130 may also be connected to an assignments computer 132 (or shift assignments computer), such as a hospital computing device or database configured to store information related to the current care team assignments within the hospital. For example, via the wired or wireless connection 133, the voice communications server 130 may receive from and/or transmit to the assignments computer 132 data indicating the bed, room, wing, and/or log-off time for a particular nurse based on messages received from the nurse's voice communications badge device 136. In some embodiments, the voice communications server 130 may be a Vocera Voice Server (e.g., Vocera Voice Server v. 4.4.2).

In various embodiments, the voice communications badge devices 136 may be portable, battery-powered, lightweight, wireless devices that may be carried and used by various personnel within the hospital. For example, nurses, nurse assistants, doctors, and administrators may each carry or wear a voice communications badge device 136 when within the hospital. For example, each voice communications badge device 136 may be capable of voice communications when within the transmission range of any access point of the hospital (e.g., within a 35-meter to 100 meter range of wireless access points associated with the voice communications server 130, etc.). The voice communications badge devices 136 may support hands-free, near full duplex voice communications using a small microphone and a speaker. In some embodiments, in addition to the wireless communications, each voice communications badge device 136 may be capable of receiving text pages (e.g., using a pager receiver, an e-mail client, a browser application, etc.). In some embodiments, the voice communications badge devices 136 may be used as one-way text pagers anywhere within the coverage area of a global pager service network.

The sync server 110 may be one or more server computing devices configured to at least synchronize care team assignment data from different systems related to the hospital. In particular, the sync server 110 may be configured to continually receive data from both the EHR server 120 and the voice communications server 130 that indicates up-to-date changes to care teams associated with the various patients, locations, and/or shifts of the hospital. For example, the sync server 110 may receive subscription messages from the voice communications server 130 indicating when particular nurses of the hospital log-in or out of a shift and/or HL7 messages from the EHR server 120 that indicate when a particular patient's data changes (e.g., assigned to a new bed, room, specialist doctor, etc.). The sync server 110 may be connected to a local database, such as the MySQL module 116 configured to store data records related to the various patients admitted to the hospital and/or the various care teams active in the hospital. For example, the MySQL module 116 may be accessed via the wired or wireless connection 117 to obtain a data record indicating the last known nurse, nurse assistant, bed, wing, building, physician, specialist, and hospitalist for a particular patient identifier. In some embodiments, the data within the MySQL module 116 may be formatted or otherwise configured based on data standards utilized by the voice communications server 130 as opposed to the EHR server 120.

The sync server 110 may also be connected to an HL7 log module 118, such as a local database or a file system that is configured to store information related to data feeds and HL7 messages originally transmitted from the EHR server 120. For example, via the wired or wireless connection 119, the sync server 110 may transmit to the HL7 log module 118 data describing incoming HL7 messages from the EHR server 120 or alternatively from an EHR interface engine configured to relay data feeds from the EHR server 120.

In some embodiments, the sync server 110 may utilize an architecture designed to utilize data feeds from the EHR server 120 that are delivered to the sync server 110, such as via an ADT message-handling system or software. The architecture may include a feed table that may be an HL7 service thread within a synching application or functionality executing on the sync server 110. In other words, the feed table may be a data feed configured to receive HL7 messages. The following is an illustration of how the sync server 110 may use such an architecture. When a synching application begins executing on the sync server 110, a HL7 server instance may be created for each row in the feed table. The feed table may define the inbound port on which the sync server 110 may listen for an incoming HL7 connection (or data feed) from the EHR server 120. Once an HL7 connection is established on a port defined by the feed table, the feed table row may define a transformation (e.g., using normalizers) to convert HL7 message data from the HL7 connection into a location and patient within the synching application.

In some embodiments, such a feed table may be generally associated with HL7 message parsing functionalities of the sync server 110. For example, when an HL7 message arrives from the EHR server 120, the message may be inserted into a message table that is linked to the feed table from which the message came. Once inserted into the message table, the HL7 message may be acknowledged, processed for patient assignment information, and then processed for staff assignments information. In some embodiments, when an HL7 message arrives at the sync server 110, a feed handler may be invoked in a synchronous fashion that inserts the HL7 message into the message table and parses ROL segments of the HL7 message for storage in a role table which causes the related HL7 message to be acknowledged by the sync server 110. Once a message has been stored in the message table and acknowledged, the sync server 110 may asynchronously perform various message processing tasks in order to continue reading and acknowledging messages. In some embodiments, the sync server 110 may read a message from a database and apply a field mapping/rule set to populate the columns of the message table.

In some embodiments, the sync server 110 may be configured to perform patient assignment operations that populate local data from HL7 message data. For example, in response to receiving an incoming HL7 message, the sync server 110 may parse the message using normalizing operations, such as described below with reference to FIGS. 7A-7C in order to identify a patient identifier, patient assigned location, and patient prior location. The sync server 110 may then perform a look-up operation using the patient identifier on a local database and update the patient information (e.g., physician data, assigned bed, etc.) of the local database with any new information from the received HL7 message.

In some embodiments, the sync server 110 may also populate an expression evaluator (e.g., MVFLEX Expression Language (MVEL) expression evaluator) with data representing the assigned location, prior location, and patient, and execute an ADT event expression for the HL7 message that causes the locations to be updated, either by assigning the patient to the location, removing the patient from the location, or moving (transferring) the patient from the prior location to the assigned location.

In some embodiments, in response to receiving an event message from the EHR server 120, the sync server 110 may also update a link table to contain the feed identifier, message identifier, prior patient location, assigned patient location, and patient identifier. In some embodiments, message processing operations by the sync server 110 may produce both events that indicate patient location changes (or assignment events) and staff location changes (or staff assignment events).

In some embodiments, the sync server 110 may be configured to update local data to indicate care team assignment changes as indicated by event messages from the voice communications server 130. For example, when a patient location has changed (e.g., reassigned to a new bed/room/wing, etc.), the sync server 110 may update local database records to remove nurse assignments to the patient (or his/her location) and insert new nurse assignments to the patient based on his/her new location from the current message. As another example, when a patient location has not changed, the sync server 110 may check for updates to care team assignments in the ROL segments of an incoming subscription message by comparing data in the ROL segments from the prior message to the current subscription message.

In some embodiments, the sync server 110 may specify and adjust over time the locations and roles of personnel associated with care team assignments of the hospital by creating unit location entries in a local database when synchronizing with the voice communications server 130 and/or the EHR server 120. For example, the sync server 110 may download all group data indicating various care team assignments of the hospital from the voice communications server 130 and run each downloaded group through a predefined template which is associated with a unit in the hospital. If the template is a match, the results from applying the template are processed using location and role normalization operations for the unit. If both normalization operations produce matching results, then the group may become associated with that unit, location and role. In addition, the source (or "source of truth") may be specified as the voice communications server 130. In some embodiments, the sync server 110 may also create unit role entries (e.g., data records) during an initial synchronization process with the voice communications server 130. In some embodiments, the sync server 110 may insert a "unit role" data record into a table associated with the voice communications server 130 for each role successfully mapped by the template for the unit. For example, for each voice communications server 130 assignment source (e.g., data record data field showing a source) inserted, the sync server 110 may also insert an additional source data field for a unit role for the feed that indicates the assignment source as the source, as the unit is tied to the feed. In some embodiments, the sync server 110 may store in memory a pointer for each role created or matched groups to role mappings that may be used when assignment change events are generated asynchronously.

In some embodiments, the sync server 110 may recognize and store data indicating care team member assignments (e.g., staff assignments) using an interface library executing on the sync server 110. Such a library may make an HTTP connection to a process (e.g., a Tomcat process) running on the voice communications server 130 and may further register for group membership change events (i.e., subscribe to receive event messages from the voice communications server 130). For example, when an event occurs related to the reassignment of a care team member, the sync server 110 via the library may receive a notification of the event, causing the library to look-up a related group-to-location and role mapping created during an initial process, and send an update message to the EHR server indicating such a reassignment.

In some embodiments, assignments may be stored in an assignment table in a local database. The assignment table may contain role identifiers, location identifiers, and the user identifiers (e.g., unique identifiers for each nurse, etc.) wherein the role identifier may be the source, unit and role from which the assignment was generated. In some embodiments, each role data record may include a set of rules.

In some embodiments, the sync server 110 may be a virtual machine, module, logic, application, circuitry, or other functionality for executing synching software that may be executed on or otherwise supported by a server computing device associated with the hospital, such as the voice communications server 130.

FIGS. 2A-2B illustrate exemplary data that may be received at an embodiment sync server from various sources for processing in order to identify accurate and complete care team assignment data. The data may be received via various communication pathways, such as via messaging via the Internet, a local area network (LAN), etc.

FIG. 2A illustrates an exemplary data structure 202 (or data record) including care team assignment data from a voice communications server that may be received by an embodiment sync server. The data structure 202 may include various data segments 210-222, including a location identifier segment 210, a nurse role segment 212, a nurse assistant role segment 214, a primary doctor role segment 216, a specialist doctor role segment 218, a hospitalist role segment 220, and an optional patient identifier segment 222. In general, the role segment (or role identifier segment) for any type of doctor or physician may be referred to as a physician role segment. As the data structure 202 may be received from the voice communications server, it may be considered to include location-based and/or shift-based care team assignment data, and thus may be assumed to include accurate, up-to-date data for care team members that are location-based and/or shift-based. For example, data related to nurses, nurse assistants, and other shift or location-based hospital workers from the data structure 202 may be more trusted or relied upon by the sync server when executing embodiment synchronizing operations. In other words, the voice communications server may typically (but not always) be determined as the "source of truth" for shift-based and/or location-based care team assignment data.

As shown in FIG. 2A, the location identifier segment 210 may include data indicating the care team assignment data corresponds to a "Room 1", the nurse role segment 212 includes data indicating the current nurse assigned to Room 1 is "Nancy", and the nurse assistant role segment 214 includes data indicating the current nurse assistant assigned to Room 1 is "Allen." As the data structure 202 may be received from the voice communications server, the data structure 202 may or may not include any useable data in the data segments 216-222. In other words, the exemplary data structure 202 may include information in the data segments 216-222 that may be considered out-of-date or otherwise unusable by the sync server. For example, as a primary doctor may not be a shift-based or location-based professional, there may be no primary doctor identifier data within data segment 216. As another example, there may be a hospitalist "Hugh" indicated within the hospitalist role segment 220 that the sync server may or may not disregard. In some embodiments, the data within data segments 216-222 may be non-null and otherwise accurate; however, the receiving sync server may be configured to disregard or discount such data during synchronizing operations as the origin of the data structure 202 is the voice communications server.

In some embodiments, the data structure 202 may be received at the sync server when subscribed to receive event messages (e.g., care team assignment membership changes) from the voice communications server. In some embodiments, the data structure 202 may be received via a HTTP connection between the sync server and the voice communications server established via a proprietary API call by the sync server.

FIG. 2B illustrates an exemplary data structure 252 (or data record) including care team assignment data from an EHR server that may be received by an embodiment sync server. The data structure 252 may include various data segments 260-272, including a location identifier segment 260, a patient identifier segment 262, a nurse role segment 264, a nurse assistant role segment 266, a primary doctor role segment 268, a specialist doctor role segment 270, and a hospitalist role segment 272.

As the data structure 252 may be received from the EHR server, it may be considered to include patient-based care team assignment data, and thus may be assumed to include accurate data for the patient (e.g., assigned room, name, etc.) and the physicians associated with the patient. For example, data related to the patient and his/her long-term physicians may be more trusted or relied upon by the sync server when executing embodiment synchronizing operations. In other words, the EHR server may typically (but not always) be determined as the "source of truth" for patient-based care team assignment data).

As shown in FIG. 2B, the location identifier segment 260 may include data indicating the care team assignment corresponds to a "Room 1", the patient identifier segment 262 may include data indicating the patient's name is "Patty", the nurse role segment 264 includes data indicating a plurality of nurses that have been assigned to Patty, the primary doctor role segment 268 includes data indicating Patty's assigned primary doctor is Tom, the specialist doctor role segment 270 includes data indicating Patty's assigned specialist doctor is Sam, and the hospitalist role segment 272 includes data indicating Patty's assign hospitalist is Harry.

As the data structure 252 may be received from the EHR server, the data structure 252 may or may not include any useable data in the data segments 264-266. In other words, the exemplary data structure 252 may include information in the data segments 264-266 that may be considered out-of-date or otherwise unusable by the sync server. For example, as there are three potential nurses assigned to Patty in the data structure 252, the sync server may assume the nurse data includes data of multiple shifts or that is otherwise out-of-date, and thus not all (or none) may currently be accurate. In some embodiments, the data within data segments 264-266 may be non-null and otherwise accurate; however, the receiving sync server may be configured to disregard or discount such data during synchronizing operations as the origin of the data structure 252 is the EHR server.

In some embodiments, the data structure 252 may be received at the sync server when an EHR interface engine is registered or otherwise configured to relay HL7 data feeds from an EHR server. In some embodiments, the data structure 252 may be received via an HL7 transmission, such as via ADT message-handling software associated with an EHR interface engine.

FIGS. 3A-3B illustrate exemplary synched data that may be transmitted by an embodiment sync server to various sources for storage in individual tracking systems, such as EHR and voice communications systems. The synched data in FIGS. 3A-3B may result from the sync server evaluating the data from both received data structures 202, 252 as illustrated above in FIGS. 2A-2B. For example, the sync server may generate the data structures 302, 352 for transmission to the voice communications server and EHR server respectively based on evaluating the data structures 202, 252 and/or any previously stored data within a local database (e.g., MySQL database).

FIG. 3A illustrates an exemplary data structure 302 (or data record) formatted for use by a voice communications server and similar to the data structure 202 illustrated above. However, unlike the data structure 202, the data structure 302 includes synched, current care team assignment data for all the data segments. The data structure 302 may include various data segments 310-322, including a location identifier segment 310, a nurse role segment 312, a nurse assistant role segment 314, a primary doctor role segment 316, a specialist doctor role segment 318, a hospitalist role segment 320, and an optional patient identifier segment 322.

Unlike the data structure 202 of FIG. 2A, the data structure 302 includes accurate data for physicians and the patient (i.e., data segments 316-322). For example, based on accurate patient-related data received in the data structure 252 from the EHR server, the sync server may add data to the primary doctor role segment 316 indicating Tom is the primary doctor for Room 1, data to the specialist doctor role segment 318 indicating Sam is the special doctor for Room 1, data to the hospitalist role segment 320 indicating Harry is the hospitalist for Room 1, and optionally data to the patient identifier segment 322 indicating Patty is the patient in Room 1.

FIG. 3B illustrates an exemplary data structure 352 (or data record) formatted for use by an EHR server and similar to the data structure 252 illustrated above. However, unlike the data structure 252, the data structure 352 includes synched, current care team assignment data for all the data segments. The data structure 352 may include various data segments 360-372, including a location identifier segment 360, a patient identifier segment 362, a nurse role segment 364, a nurse assistant role segment 366, a primary doctor role segment 368, a specialist doctor role segment 370, and a hospitalist role segment 372.

Unlike the data structure 252 of FIG. 2B, the data structure 352 includes accurate shift-based and/or location-based data for nurses and nurse assistants (i.e., data segments 364-66). For example, based on accurate data received in the data structure 202 from the voice communications server, the sync server may add data to the nurse role segment 364 indicating a single current nurse (Nancy) for Patty in Room 1 and data to the nurse assistant role segment 366 indicating Allen is the current nurse assistant for Patty in Room 1.

Figure 4A:
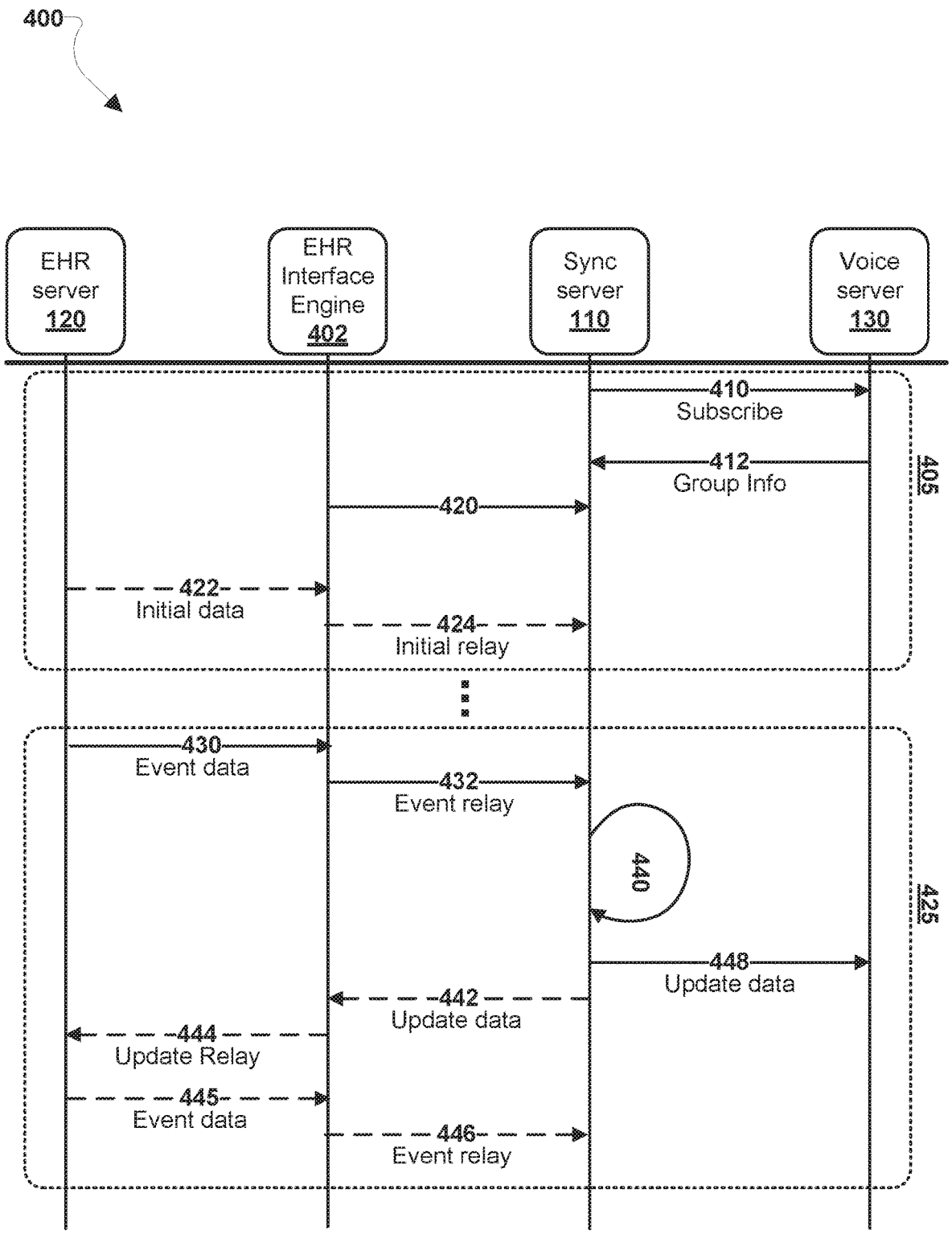
FIGS. 4A-4B are call flow diagrams that illustrate embodiment communications between a sync server, a voice communications server, and an electronic hospital record server according to various embodiments.

FIG. 4A illustrates a scenario 400 of exemplary communications between a sync server 110, a voice communications server 130, and an electronic hospital record server 120 according to various embodiments. For the purpose of simplicity, FIG. 4A illustrates communications during two phases of operation, an initialization phase 405 during which the sync server 110 connects with and otherwise registers requests for receiving up-to-date information from the other servers 120, 130, and a sync phase 425 during which the sync server 110 receives and utilizes event messages from the servers 120, 130 to generate complete, synched care team assignment data to be redistributed back to the servers 120, 130.

During the initialization phase 405, the sync server 110 may transmit a subscription message 410 to the voice communications server 130, indicating a request to receive group information. The subscription message 410 may request that any changes to care team assignment data stored at the voice communications server 130 (e.g., memberships of various care teams, etc.) be reported to the sync server 110 at the time of their occurrence. For example, such a subscription may cause the voice communications server 130 to transmit an event message to the sync server 110 in response to detecting that a nurse has logged out of his care team assignment for the day (e.g., at the end of a shift).

In some embodiments, the subscription message 410 may create a HTTP connection to a process running on the voice communications server 130 such that when an event occurs that changes care team assignments, the sync server 110 is notified of the event and any related changes to care team assignments.

In some embodiments, the subscription message 410 may request notifications for all or a portion of the care team assignments data (or data records) maintained by the voice communications server 130. For example, the subscription message 410 may register the sync server 110 to receive messages indicating any change to any care team assignment within a hospital, or alternatively to receive messages indicating changes only involving a set of care team assignments for a certain wing of the hospital, etc.

In some embodiments, the sync server 110 may subscribe to the voice communications server 130 using calls from a proprietary application programming interface (API). For example, instead of utilizing a human web console, the sync server 110 may utilize calls via a programmatic interface, such as a Vocera Administration Interface (VAI).

In response to receiving the subscription message 410, the voice communications server 130 may transmit group information data 412 to the sync server 110. Such group information data 412 may include data indicating the various groups stored by the voice communications server 130, such as groups comprising a location (e.g., a room number, etc.), patient(s) name(s), care team members assigned to the location, etc. For example, the group information data 412 may include a plurality of data records, each associated with various rooms of a hospital and indicating any currently known identities of assigned nurses, nurse assistants, physicians, patients, hospitalists, etc. for the rooms. The returned group information may be stored and otherwise used at the sync server 110, such as stored in a local database (e.g., MySQL database). In some embodiments, the sync server 110 may perform some normalization operations, such as described herein, on data within the received group information data 412 from the voice communications server 130.

The EHR interface engine 402 may also transmit a message 420 to the sync server 110 that indicates push notifications that report or relay incoming EHR event messages may be sent to the sync server 110 from the EHR interface engine 402. In other words, the EHR interface engine 402 that is configured by a subscribing entity (e.g., a hospital) may connect to the sync server 110 to deliver any updated message related to assignments. For example, the message 420 may indicate codes or identifiers of rooms, patients, nurses, and/or other care team assignment participants about which the sync server 110 may receive notifications reporting any subsequent changes (e.g., re-assignments, personnel changes, admittances, etc.). The EHR interface engine 402 may store information for use in determining whether to relay particular data feeds received from the EHR server 120 to the sync server 110. In some embodiments, the EHR interface engine 402 may be a module, application, routine, and/or other functionality supported on a distinct device, such as networked computer, or alternatively supported within the sync server 110. In some embodiments, the EHR interface engine 402 may be a TCP/IP interface.

At some time during the initialization phase 405, the sync server 110 may receive initial EHR data from the EHR interface engine 402 for storage in a local database (e.g., MySQL database). With initial data, the sync server 110 may build patient census, but may not have an entire data set for patients. In some embodiments, such initial EHR data may be received in response to the EHR server 120 transmitting initial data 422 to the EHR interface engine 402, which in turn transmits initial relay messages 424 to relay the initial data 422 to the sync server 110 via HL7 messages. Such initial data 422 may not be transmitted by the EHR server 120 on demand, but may instead be sent in response to a regular event encountered at the EHR server 120, such as an update to patient data (e.g., room change, discharge, etc.). The initial data 422 may include all relevant or known patient-based data for a patient associated with a change at the EHR server 120. Further, such initial data 422 may or may not include data associated with more than just the care team assignment data that are changed due to the regular event encountered at the EHR server 120. For example, the initial data 422 may include data records related to a plurality of patients currently admitted in the hospital or alternatively may only include data records of the patients currently admitted in the hospital that have had a change in their care team assignments (e.g., room change, specialist doctor change, etc.).

At some later time during the sync phase 425, the EHR server 120 may encounter a patient-related event. For example, a hospital worker may use a terminal to update records stored on the EHR server 120 to indicate a certain patient has been admitted, discharged, changed rooms, been assigned a new or different specialist, been assigned a new or different hospitalist, etc. In response, the EHR server 120 may transmit event messages 430 (or update data feeds) to the EHR interface engine 402 for distribution to various devices. The event messages 430 may include data records related to various patients associated with a hospital, and further may include other data associated with the patients, such as data indicating primary care physicians and room assignments for the patient within the hospital.

The transmission by the EHR server 120 of the event messages 430 may be triggered by the occurrence of the event, and thus may not be invoked by outside entities, such as via request messages from the EHR interface engine 402, sync server 110, etc. In other words, the sync server 110 or the EHR interface engine 402 may not actively (or in an on-demand manner) read data currently stored at the EHR server 110, but may instead may be required to wait to receive event messages 430 from the EHR server 120 as events occur. For example, every time a transaction occurs, such as a patient being reassigned to a new hospital bed or room, the EHR server 120 may transmit a new event message 430.

In response to receiving the event messages 430, the EHR interface engine 402 may transmit relay event messages 432 to the sync server 110. For example, the EHR interface engine 402 may transmit data to the sync server 110 indicating that a data record was received from the EHR server 120 that relates to a patient of the hospital associated with the sync server 110 (e.g., a record indicating that a particular patient name was admitted to the hospital and will be within a certain room number and cared for by a particular, physician, etc.). In some embodiments, the event relay messages 432 may correspond to a registration of the EHR interface engine 402 to provide HL7 messages to the sync server 110. For example, the EHR interface engine 402 may only transmit event relay messages 432 to the sync server 110 when the included data of the event message 430 relates to a patient with which the sync server 110 is pre-associated. In some embodiments, the sync server 110 may receive HL7 messages regarding all patients of the hospital unless the EHR interface engine 402 is configured to perform filtering to remove certain HL7 messages. In some embodiments, the event relay messages 432 may be HL7 messages sent via HL7 message-handling software.

In response to receiving the event relay messages 432 from the EHR interface engine 402, the sync server 110 may perform various operations 440 to process the received data. In particular, the sync server 110 may evaluate records reported in the received event relay message 432 from the EHR interface engine 402 against the group information data 412 from the voice communications server 130. For example, the sync server 110 may use a room identifier (e.g., "Room 1") from the event relay message 432 to perform a lookup in a MySQL database of group information data to retrieve a data record for a patient assigned to the room.

Based on a comparison of data from the EHR server 120 and the voice communications server 130, the sync server 110 may determine whether updates are needed to be sent to the EHR server 120 and/or the voice communications server 130. For example, if nurse identifiers received from the event relay message 432 were inaccurate or incomplete, the sync server 110 may determine that an update to the EHR server 120 is needed. As another example, if physician data received from the group information data 412 was out incomplete or out-of-date, the sync server 110 may determine that an update to the voice communications server 130 is needed.

In some embodiments, the operations 440 may include the sync server 110 performing a lookup of a group-to-location and role mapping that was created during the initialization phase 405 based on the group information data 412 received from the voice communications server 130.

When inaccurate or out-of-date data is detected in the data received from the voice communications server 130 and/or the EHR server 120, the sync server 110 may generate an assignment event that causes the sync server 110 to transmit updates to the servers 120, 130 having data in need of adjustment. In particular, if changes are needed to the data currently stored at the voice communications server 130, the sync server 110 may transmit an update message 448 to the voice communications server 130 that is configured to cause the voice communications server 130 to replace, delete, add, and/or otherwise update care team assignment data according to the determinations of the sync server 110. For example, the sync server 110 may transmit an update message 448 indicating that a data record needs to add a member (e.g., a patient has been moved to a room associated with a nurse, etc.) and/or remove a member (e.g., a patient is no longer associated with a particular room worked by a nurse, etc.).

The update message 448 may be transmitted via an API call, such as using a VAI communication. In some embodiments, the update message 448 may be an "addMember" or a "removeMember" API call, such as defined in the VAI API. In some embodiments, the voice communications server 130 may be configured to transmit messages indicating any changes to the care team assignment data to other devices, such as a staff assignment database or device. For example, such messages may be reflected on a user interface application that displays user assignments (e.g., information showing location and role changes or current assignments, etc.) to a group.

In the scenario 400 illustrated in FIG. 4A, the sync server 110 may not need to update the EHR server 120 as the EHR server 120 may already store the most up-to-date patient-related data (i.e., the sync operations 440 are performed in response to the events originally reported by the EHR server 120). However, if changes are indeed needed to the data currently stored at the EHR server 120 as well as the data at the voice communications server 130, the sync server 110 may transmit an update message 442 to the EHR interface engine 402 that is configured to cause the EHR interface engine 402 to transmit an update relay message 444 to the EHR server 120. Such an update relay message 444 may cause the EHR server 120 to replace, delete, add, and/or otherwise update care team assignment data according to the determinations of the sync server 110. For example, the update relay message 444 may include data indicating that a patient associated with a particular hospital bed is now being cared for by a particular nurse and nurse assistant care team, and thus data currently stored at the EHR server 120 for such care team assignment needs to be updated. In some embodiments, the update message 442 and/or the update relay message 444 may or may not be HL7 messages.

As the EHR server 120 is generally configured to transmit event messages in response to detecting events that change care team assignment data, the EHR server 120 may transmit an event message 445 to the EHR interface engine 402 in response to receiving and processing the update relay message 444. The EHR interface engine 402 may in turn transmit an event relay message 446 to the sync server 110. However, as the data included in the event relay message 446 is the result of the operations 440 performed by the sync server 110, the sync server 110 may simply disregard the event relay message 446. Alternatively, the sync server 110 may be configured to perform the operations 440 with regard to the event relay message 446; however, as the data of the event relay message 446 is already accounted for, no new updates may be determined by the sync server 110.

In some embodiments, the sync server 110 may perform normalizing operations to ensure that data exchanged with the EHR interface engine 402 is in a format that may be accessible to the EHR server 120. For example, in response to receiving the event relay message 432, the sync server 110 may transform the included data in order to properly make comparisons between the EHR information and other data stored at the sync server 110, such as care team assignment data received from the voice communications server 130. As another example, update messages 442 may include updates to care team assignments that have been reformatted for use by the EHR server 120 (i.e., generated using reverse normalization operations).

In some embodiments, the sync server 110 may be configured to store log information (e.g., data within an HL7 log database, etc.) in response to every HL7 communication exchanged with the EHR interface engine 402. For example, in response to receiving the initial relay message 424 and/or any event relay message 432, as well as in response to transmitting any update message 442, the sync server 110 may store a record of the time, recipient, content, and/or content of such an HL7 transmission in an HL7 log file. Similarly, in some embodiments, the voice communications server 130 may be configured to store log information (e.g., data within a log database, etc.) in response to every communication exchanged with the sync server 110. For example, in response to receiving the initial subscription message 410 and/or any update message 448, as well as in response to transmitting any group information data 412, the voice communications server 130 may store a record of the time, recipient, content, and/or content of such a transmission in a log file.

The following is an illustrative scenario in accordance with the exemplary communications of FIG. 4A. During the initialization phase 405, the sync server 110 may receive initial care team assignment data from the EHR server 120 indicating that a Patient A is assigned to Room 123, a Nurse B, and Specialist D. The voice communications server 130 may store care team assignment data that indicates the Nurse Z is assigned to Room 123 and currently logged in. During the sync phase 425, the sync server 110 may receive an event relay message 432 from the EHR interface engine 402 indicating that Patient A has been reassigned to Specialist F. In response, the sync server 110 may determine that based on the initial group information data 412 received from the voice communications server 130, an update message 442 may be sent to the voice communications server 130 in order to update care team assignment data to reflect that Specialist F is now associated with Room 123 and Patient A. Further, the sync server 110 may transmit an update message 442 to the EHR interface engine 402 in order to update care team assignment data at the EHR server 120 to reflect that Room 123 is associated with Nurse Z, not Nurse B.

Figure 4B:
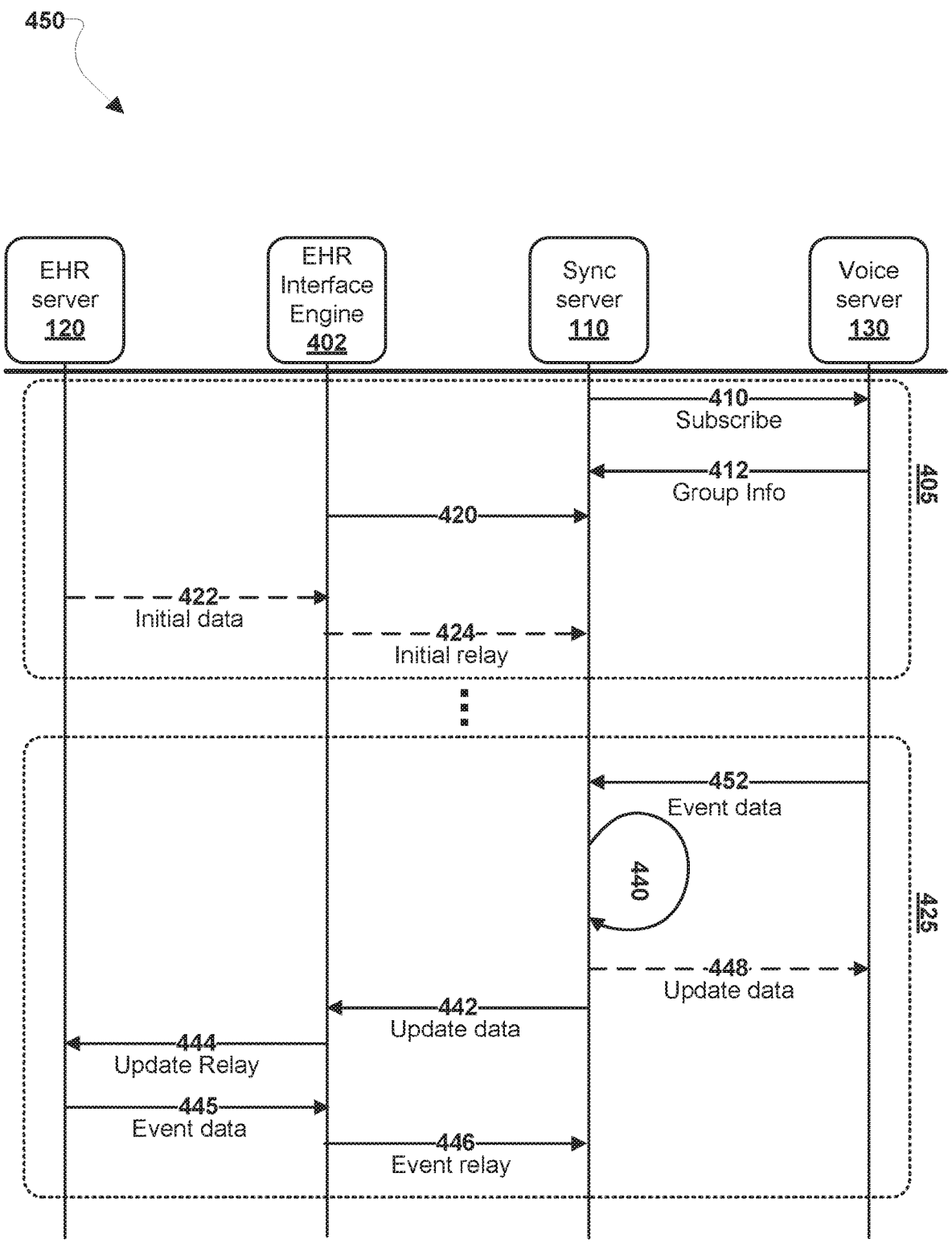

FIG. 4B illustrates a scenario 450 of exemplary communications between a sync server 110, a voice communications server 130, and an electronic hospital record server 120 according to various embodiments. The scenario 450 illustrated in FIG. 4B is similar to the scenario 400 illustrated in FIG. 4A, except that in the scenario 450 synchronization operations 440 may be performed by the sync server 110 in response to receiving event messages 452 from the voice communications server 130 via an established HTTP connection. For example, the sync server 110 may compare the care team assignment data received via the event message 452 to previously received care team assignment data (e.g., data from the initial relay message 424, etc.) to determine whether the EHR server 120 needs to be updated to reflect the changes encountered at the voice communications server 130. If the sync server 110 determines the EHR server 120 should be updated in response to the event message 452, the sync server 110 may transmit the update message 442 to the EHR interface engine 402 as described above. In some embodiments, the sync server 110 may perform normalization operations on the data from the received event messages 452.

In the scenario 450, the sync server 110 may not need to update the voice communications server 130 as the voice communications server 130 may already store the most up-to-date care team assignment changes (i.e., the sync operations 440 are performed in response to the events originally reported by the voice communications server 130). However, if changes are needed to be made to the data stored at the voice communications server 130 as well, the sync server 110 may transmit the update message 448 to the voice communications server 130, such as via a VAI API call.

The following is an illustrative scenario in accordance with the exemplary communications of FIG. 4B. During the initialization phase 405, the sync server 110 may receive initial care team assignment data from the EHR server 120 indicating that a Patient A is assigned to Room 123, a Nurse Z, and Specialist D. The voice communications server 130 may store care team assignment data that indicates the Nurse Z is assigned to Room 123 and currently logged in. During the sync phase 425, the sync server 110 may receive an event message 452 from the voice communications server 130 indicating that Nurse Z has been replaced with Nurse Q (e.g., Nurse Z's shift is over and he has logged out using his voice communications badge device, etc.). In response, the sync server 110 may determine that based on the initial data received from the EHR server 120, an update message 442 must be sent to the EHR interface engine 402 for relay to the EHR server 120 in order to update care team assignment data at the EHR server 120 to reflect that Room 123 is now associated with Nurse Q. Further, the sync server 110 may also transmit the update message 448 to cause the voice communications server 130 to update care team assignment data to reflect that, in addition to Nurse Q, Room 123 is associated with Patient A and Specialist D.

Figure 5A:
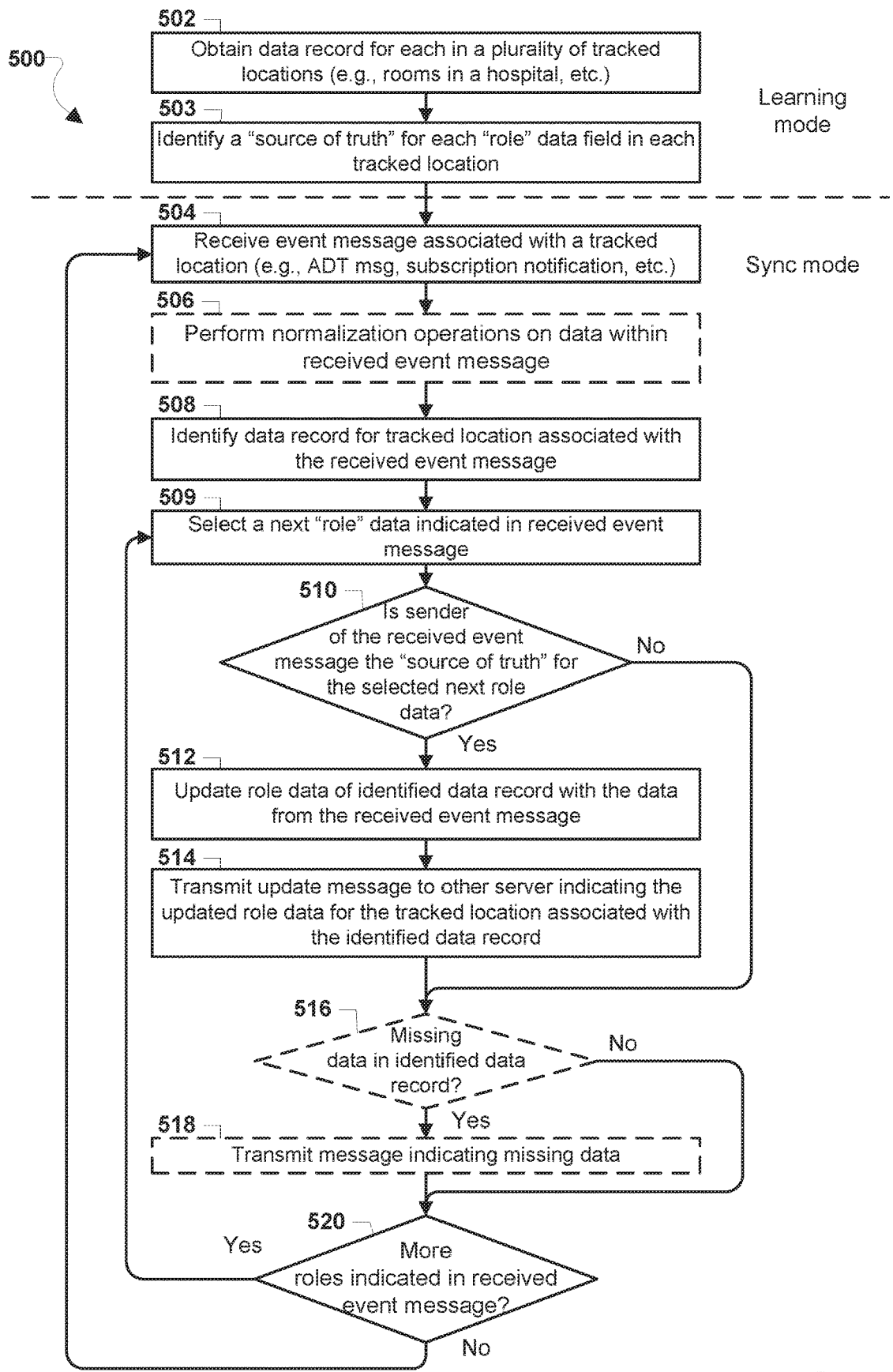
FIGS. 5A-C are process flow diagrams that illustrate embodiment methods performed by a sync server to provide up-to-date information of current care team assignments based on data from other servers (e.g., a voice communications server and/or an electronic hospital record (EHR) server).
Figure 5B:
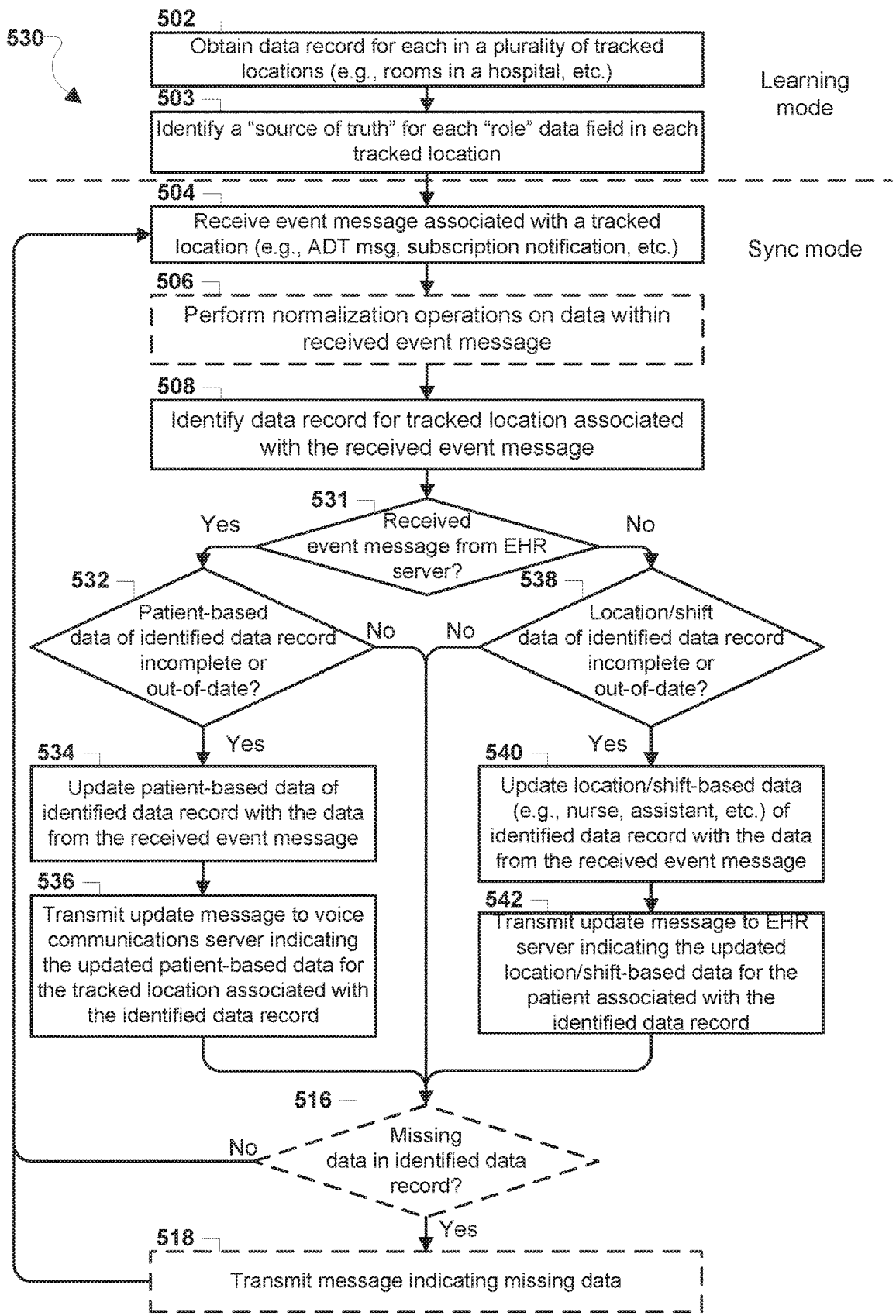
Figure 5C:
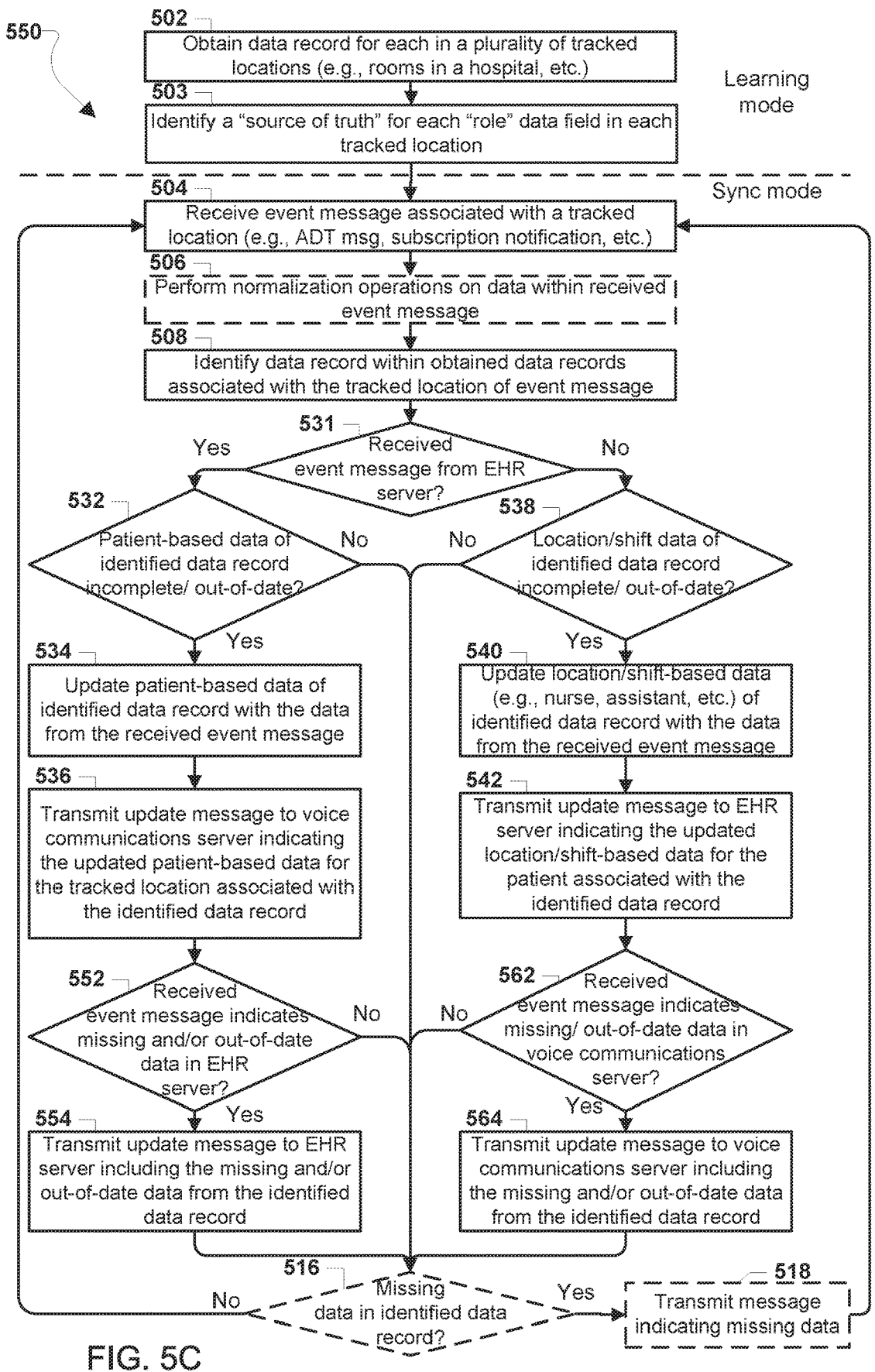

In various embodiments, a processor of an embodiment sync server may be configured to perform a process for synchronizing care team assignment data of a hospital (or other similar facility). For example, such a process may include operations for obtaining a data record for each in a plurality of tracked locations of the hospital (e.g., retrieving available, previously stored/received care team assignment data for the hospital from a local database), receiving an event message associated with a certain tracked location of the hospital from a remote server (e.g., an HL7 message from an EHR server, an update from a voice communications server, etc.), determining whether data in an obtained data record for the certain tracked location is inaccurate based on the received event message from the remote server (e.g., wrong nurse identified for a patient/room, etc.), and transmitting an update message to another remote server in response to determining the care team assignment data that is stored at the another remote server and that is associated with the certain tracked location is inaccurate based on the received event message. FIGS. 5A-5C illustrate embodiment methods 500, 530, 550 that are similar to this general process, but that also include more detailed operations.

FIG. 5A illustrates an embodiment method 500 performed by a sync server to provide up-to-date information of care team assignments based on data from other servers (e.g., a voice communications server and/or an EHR server). The operations of blocks 502-503 may represent an "offline" learning mode wherein the sync server may obtain data records and identify the server (e.g., EHR server, voice communications server, etc.) that may be defined as the "source of truth" for each role in each unit (e.g., room(s) of a hospital, etc.) represented in the obtained data records. In other words, prior to receiving event messages from the EHR server and/or the voice communications server, the sync server may perform operations in an offline mode to collect data records representing each unit in the hospital and determine which server of the EHR server or the voice communications server has and will subsequently provide accurate information (i.e., updates) related to the various roles for the various units. For example, for data records associated with each hospital room of the hospital, the sync server may process all available data about various roles, such as nurses and/or nurse assistants, patients, hospitalists, doctors, etc., to identify whether the data from the EHR server or the voice communications server is accurate for each role. As another example, for a data record for a certain room, the EHR server may be identified as the source of truth for data for a first role (e.g., a patient identifier) and the voice communications server may be identified as the source of truth for data for a second role (e.g., nurse identifier, etc.).

Accordingly, in block 502, the sync server may obtain a data record for each in a plurality of tracked locations, such as a data record for each room in a hospital. Such data records may be received from a local database, such as a MySQL database and/or another data source, such as a download from another server (e.g., voice communications server, etc.). In general, the obtained data records may include a database of common terms that represent an initial state of all the care team assignments associated with the tracked locations. For example, the obtained records may indicate the various parties assigned to each room of the hospital at a given time, the patients associated with the rooms, related physicians, etc.

In some embodiments, the obtained data records may correspond to group information received from the voice communications server, such as an initial download of current shift-based and/or location-based care team assignment data for all relevant, tracked locations within a hospital. In some embodiments, the obtained data records may be records previously generated or otherwise populated by the sync server (e.g., synched care team assignment data based on data from both the voice communications server and the EHR server).

In block 503, the processor of the sync server may identify a "source of truth" for each "role" data field in each obtained tracked location data record. In other words, the sync server may determine which of the EHR server and the voice communications second server may be the provider of accurate, up-to-date information for every role for each of the obtained data records, wherein the determinations includes performing an offline, learning analytics routine. For example, for each of the data records associated with the units of the hospital (e.g., room(s), etc.) obtained with the operations of block 502, the sync server may perform an offline, learning analytics routine (or heuristics analysis) that determines a source of truth per role (e.g., nurse, nurse assistant, patient, hospitalist, etc.) for each data record. For example, such a training/learning mode or routine may be executed that iterates through data records to calculate a server or system that has the highest probability of providing the most up-to-date or accurate information for each role (e.g., hospitalist, nurse, nurse assistant, etc.) in each location/unit of the hospital that may be tracked by the sync server. For example, the operations of block 503 may include analysis operations that provide accuracy assessments or reports for each role for each unit of the hospital, wherein the reports indicate which of the EHR server and the voice communications server has a higher accuracy for providing up-to-date data for that particular role for that particular unit, and thus may be determined the source of truth for that particular role within that particular unit of the hospital.

The EHR server or the voice communications server may be determined the source of truth for any role within any unit of the hospital based on the analysis of block 503. In other words, regardless of identification trends, the learning analytics routines may identify either the EHR server or the voice communications server based on the evaluation of data records available to the sync server at a given time. For example, even if the EHR server is typically identified as the source of truth for patient-based data, the sync server may identify the voice communications server as the source of truth for particular patient-based data of a particular tracked location in the hospital. Similarly, even if the voice communications server is typically identified as the source of truth for shift or location-based data, the sync server may identify the EHR server as the source of truth for particular shift or location-based data of a particular tracked location in the hospital.

The operations of blocks 504-520 may represent a "live" (or online or real-time) sync mode wherein the sync server may continually update data records based on received messages from the voice communications server and/or the EHR server. For example, based on offline learning mode operations, the sync server may have previously identified that the EHR server is the source of truth for patient information for a certain room. When in receipt of a subsequent event message from the EHR server that includes a patient identifier for the certain room, the sync server may update locally stored data for the patient identifier for that certain room and transmit an update message to the voice communications server to update data to correspond with the accurate identifier data provided by the EHR server. Accordingly, in block 504, the sync server may receive an event message associated with a tracked location, such as an HL7 message from an EHR interface engine, a subscription notification from the voice communications server, etc. For example, based on a subscription with the voice communications server to receive any care team assignment changes (e.g., nurse log-ins, log-outs, etc.), the sync server may receive a notification via an HTTP connection that indicates the care team for a certain tracked room within the hospital has changed due to a new shift beginning (e.g., day shift turning to night shift, etc.). As another example, the event message may be an HL7 message received via HL7 message-handling software (e.g., from an EHR interface engine) indicating that a new patient has been admitted or discharged from a certain room, wing, and/or the entire hospital. The event message may indicate various identifiers, codes, names, labels, and/or similar data related to care team members, locations within the hospital, patient and patient associations with care team members and/or locations within the hospital, timestamps, and/or other data that may be used by the sync server to properly contextualize the event message's information.

In optional block 506, the sync server may perform normalization operations on data within the received event message. In general, such normalization operations may adjust the formatting, organization, and/or content of some or all of the information within the received event message to conform to a uniform data configuration used by the sync server. For example, when the event message is an HL7 message the sync server may adjust some data within the message to be structured according to data formatting standards predefined by the sync server so that direct comparisons may be made between data from the HL7 message and data previously received and processed from the voice communications server. As another example, when the received event message is from the voice communications server, the sync server may perform operations to transform included group information for comparisons with stored data (e.g., data previously received from the EHR server, etc.). Additional descriptions of normalization operations are illustrated below with reference to FIGS. 7A-7C. In some embodiments, the normalization operations may include the sync server translating data fields of the received event message using an intelligent translator into common terms that are can be compared to the information of another data source. For example, the translator may convert HL7 message data from the EHR server into a format or structure similar to the data used by the voice communications server, and/or vice versa.

In block 508, the sync server may identify a data record within the obtained data records associated with the tracked location of the received event message. For example, the sync server may perform a look up using a location identifier (e.g., room 123, etc.) within the received event message to identify the data record that also corresponds to the location identifier. In some embodiments, the identified data record may be a data record that includes various data field as currently stored or otherwise reported by both the EHR server and the voice communications server. For example, the identified data record may include all data from the EHR server and the voice communications server that is related to the room associated with the event message, such as the current data fields for a hospitalist associated with a Room #123 as reported by both the EHR server and the voice communications server, if available. In some embodiments, the identified data record may only include certain data fields from one server or the other, as the other server may not currently store or report such data. For example, when the hospitalist for a Room #123 has not previously been stored by the voice communications server, the identified data record may only include the hospitalist data field as reported by the EHR server.

In block 509, the processor of the sync server may select a next "role" data (or identifier data field) indicated in received event message. In other words, the sync server may iteratively evaluate and update data for one or more roles (or identifiers) that are indicated in the received event message. For example, when the received event message includes updates to one or more nurse identifiers, a nurse identifier and a hospitalist identifier, and/or any other combination of updated information for a certain room of the hospital, the sync server may select and evaluate each identifier iteratively. In determination block 510, the processor of the sync server may determine whether the server that sent the received event message is the "source of truth" for the selected next role data based on the previously-executed, learning mode operations of block 502-503. In response to determining that the server that sent the received event message is the "source of truth" for the selected next role data (i.e., determination block 510="Yes"), the processor of the sync server may update role data of the identified data record with the data from the received event message in block 512. In other words, since the role data of the received message likely is from the source of truth for that role for that particular unit in the hospital, the sync server may determine the event message indicates a valid update that should be propagated in all servers. In block 514 the processor of the sync server may transmit an update message to other server that did not transmit the received event message that indicates the updated role data for the tracked location associated with the identified data record. For example, when the selected role data is for a nurse identifier for a Room 'A' received in a message from the voice communications server, and the voice communications server has been predetermined to be the source of truth for nurse roles in Room A, the sync server may transmit the update message to the EHR server.

As another example, the sync server may determine the voice communication server is the source of truth for a nurse role for a particular unit in the hospital (e.g., an intensive care unit of the hospital referred to as 'NICU'). If, at the voice communications server, a user is assigned to the group "4 West Room 101 Bed A Nurse" (wherein "4 West" may be the intensive care unit of the hospital referred to as 'NICU'), then the sync server may insert an assignment in an assignment table with the user id, unit-role id (e.g., "NICU", "Nurse"), and unit-location id (e.g., "NICU", "Room 101A"). The sync server may then sync this assignment with other systems as the voice communication server has been identified as the source of truth for the nurse role for that particular unit. As another example, the sync server may create an 'addMember' request to add a member to a group when an HL7 message (i.e., the ADT message) from the EHR server is received and the EHR server is the source of truth for that role and unit. For those users removed, the sync server may create a 'removeMember' request to remove the user from the group. When the data from the voice communications server is the source of truth, the sync server may create an HL7 update message with the updated member.

In response to determining that the server that sent the received event message is not the "source of truth" for the selected next role data (i.e., determination block 510="No"), or in response to performing the transmitting operations of block 514, the sync server may determine whether there is any missing data in the identified data record in optional determination block 516. In some cases, after updating the local information based on received event messages, the sync server may determine that certain care team assignment data has not been provided by either the voice communications server or the EHR server. For example, after receiving a subscription message from the voice communications server and/or an HL7 message from the EHR server, the sync server may determine that its local data record for a particular patient does not include any data related to the patient's current hospitalist, family practitioner, and/or nurse assistant. Although these pieces of information may not be required (e.g., simply when no nurse assistant has been assigned or needed, etc.), the sync server may be configured to recognize the missing data if inadvertently omitted in either system. In response to determining there is missing data in the identified data record (i.e., optional determination block 516="Yes"), the sync server may transmit a message indicating the missing data in optional block 518. For example, the sync server may transmit a message to the voice communications server and/or EHR server indicating data may be missing in the stored records of the respective devices.

In response to determining there is no missing data in the identified data record (i.e., optional determination block 516="No"), or in response to performing the transmitting operations of optional block 518, the processor of the sync server may determine whether there are more roles indicated in the received event message associated with the tracked location in determination block 520. In response to determining that there is more role data to evaluate from the received event message (i.e., determination block 520="Yes"), the sync server may continue by selecting the next role in block 509. In response to determining that there is no more role data to evaluate from the received event message (i.e., determination block 520="No"), the sync server may repeat the operations described above by again receiving event messages in block 504.

As described herein, typically, although not always, the source of truth server for patient-based data may be an EHR server and the source of truth server for location-based and/or shift-based data may be a voice communications server. For simplicity of description, FIGS. 5B-5C provide detailed embodiment operations executed by a sync server, wherein patient-based data within event messages from an EHR server is assumed to be up-to-date/accurate (i.e., EHR server is the source of truth for patient-based data), and location-based and/or shift-based data from a voice communications server is assumed to be up-to-date/accurate (i.e., voice communications server is the source of truth for location-based and/or shift-based data). However, offline learning mode operations described above with reference to FIG. 5A may identify an atypical source of truth for any particular role for any particular unit of a hospital.

FIG. 5B illustrates an embodiment method 530 performed by a sync server to provide up-to-date information of care team assignments based on data from a voice communications server and/or an EHR server. The method 530 is similar to the method 500 described above reference to FIG. 5A, except the method 530 may include operations that assume that the EHR server is the source of truth for patient-based data within received event messages. The operations in blocks 502-508, 516-518 may be similar to the operations of like-numbered blocks as described above with reference to FIG. 5A.

In determination block 531, the sync server may determine whether the received event message was transmitted from the EHR server. If the received event message was transmitted from the EHR server, the sync server may determine that patient-related information may be up-to-date within the event message, but any other data may not be accurate (e.g., shift-based or location-based care team assignment information). If the received event message was not transmitted from the EHR server, the sync server may determine that shift-based or location-based care team assignment data (e.g., nurse assignments, etc.) may be accurate, but that patient-based information (e.g., primary care physician data, etc.) may not be up-to-date.

In some embodiments, the sync server may determine whether the event message is from the EHR server originally based on a tag, flag, header, or other information within the received event message that indicate the origin as the EHR server or system. In some embodiments, the determination may be made during the operations of optional block 506 as the sync server may only perform normalization operations in response to receiving EHR system data that is not structured in a similar manner to data from the voice communications server.

In response to determining that the received event message is from the EHR server (i.e., determination block 531="Yes"), the sync server may determine whether the patient-based care team assignment data of the identified data record is incomplete and/or out-of-date in determination block 532. As the event message is received from the EHR server, the sync server may assume the patient-based data is up-to-date and otherwise accurate. For example, as the EHR server may be assumed to have the most accurate long-term information related to an admitted patient of a hospital, the sync server may determine any physician assignments indicated within HL7 messages are the most up-to-date and accurate.

The sync server may compare patient-based care team assignment data, such as the various physicians assigned to the patient (e.g., general practitioner, specialists, hospitalists, etc.) stored within the identified data record to patient-based data in the received event message to determine whether there are any discrepancies. For example, when the identified data record for the tracked location does not include any data for a specialist that is named within the received HL7 message from the EHR server, the sync server may determine the identified data record is incomplete and the voice communications server should be updated. As another example, when the identified data record for the tracked location includes a different name for a specialist for a patient named within the received HL7 message, the sync server may determine the identified data record is out-of-date.

In some embodiments, the patient-based data may include at least one of a patient identifier, a role identifier, a room identifier, and a care team member identifier. In some embodiments, the sync server may utilize a heuristic or intelligence comparison algorithm to compare care team assignment data stored in obtained data records (or common terms database) to identify incorrect or out-of-date records in data from the voice communications server. In some embodiments, the sync server may utilize a configuration attribute that indicates the source of truth system. This configuration may be determined based on an offline learning analytics mode used to determine the source of truth per role per unit, such as described above with reference to FIG. 5A. In response to determining that the patient-based data of the identified data record is out-of-date (i.e., determination block 532="Yes"), the sync server may update the patient and/or physician data of the identified data record with data from the received event message in block 534. For example, the sync server may copy newer physician data from a received HL7 message into the identified data record to update the local information.

In block 536, the sync server may transmit an update message to the voice communications server indicating the updated patient-based data for the tracked location associated with the identified data record. For example, the sync server may transmit a message to the voice communications server via an established VAI connection indicating that a specialist data field for a room or bed associated with the patient should now include data indicating the assigned specialist is "Dr. Tom". In some embodiments, the message may be an "addMember" or "removeMember" message that causes the voice communications server to add or remove data from its locally stored data records (e.g., group information) related to various care team assignment data. For example, such messages may cause the voice communications server to remove data linked to a care team member (e.g., nurse, etc.) from a particular group associated with a patient, bed, room, etc.

In response to determining that the received event message is not from the EHR server (i.e., determination block 531="No"), the sync server may determine whether the location-based and/or shift-based care team assignment data of the identified data record is incomplete and/or out-of-date in determination block 538. As the event message is received from the voice communications server, the sync server may assume the location-based and/or shift-based data is up-to-date and otherwise accurate. For example, as the voice communications server may be assumed to have the most accurate care team assignment data regarding nurses based on the real-time use of voice communication badge devices, the sync server may determine any nurse information within messages from the voice communications server are the most up-to-date and accurate.

The sync server may compare care team assignment data, such as the various nurses and nurse assistants currently assigned to a patient, already stored within the identified data record to location-based and/or shift-based data in the received event message to determine whether there are any discrepancies. For example, when the identified data record for the tracked location does not include any data for a nurse assigned to a patient's bed as indicated in the received subscription message from the voice communications server, the sync server may determine the identified data record is incomplete. As another example, when the identified data record for the tracked location includes a different name for a nurse assigned to the care team for a patient named within the event message, the sync server may determine the identified data record is out-of-date.

In some embodiments, the location-based or shift-based data may include at least one of a nurse role segment (e.g., an identifier, code, etc.) and a nurse assistant role segment (e.g., identifier, code, etc.). In some embodiments, the sync server may utilize a heuristic or intelligence comparison algorithm to compare care team assignment data stored in obtained data records (or common terms database) to identify incorrect or out-of-date records in data from the EHR server.

In response to determining that the location-based and/or shift-based data of the identified data record is out-of-date (i.e., determination block 538="Yes"), the sync server may update the care team assignment data of the identified data record with data from the received event message in block 540. For example, the sync server may copy a newer nurse identifier from a received subscription message into the identified data record to update the local information.

In block 542, the sync server may transmit an update message to the EHR server indicating the updated location-based and/or shift-based data for the tracked location associated with the identified data record. For example, the sync server may transmit an HL7 message to be relayed to the EHR server via an EHR interface engine, indicating that a nurse assistant data field for a room or bed associated with the patient should now include data indicating the assigned nurse assistant has changed.

In some embodiments, the sync server may be configured to re-format or otherwise perform operations to convert the updated assignment data into a structure used by the EHR server. In other words, the sync server may transmit a message that include care team assignment data generated using the reverse of normalization operations, such as described above with reference to optional block 506. For example, the sync server may change the number or type of digits, codes, letters, and/or other information related to the care team assignment data from the received event message in order to make that data compatible with the EHR server's native formatting, etc.

In response to determining that the patient-based data of the identified data record is not out-of-date (i.e., determination block 532="No"), or in response to determining that the location-based and/or shift-based data of the identified data record is not out-of-date (i.e., determination block 538="No"), or in response to performing the transmitting operations of block 536 or block 542, the sync server may continue with the operations of optional determination block 516 as described above with reference to FIG. 5A. In response to determining there is missing data in the identified data record (i.e., optional determination block 516="Yes"), the sync server may transmit a message indicating the missing data in optional block 518 and repeat the operations described above by again receiving event messages in block 504. In response to determining there is no missing data in the identified data record (i.e., optional determination block 516="No"), the sync server may repeat the operations described above by again receiving event messages in block 504.

In some embodiments, both the voice communications server and the EHR server may include different data for particular care team assignments. Instead of merely allowing patient-based data (e.g., a patient's physician identifier, etc.) from the EHR server to overwrite different patient-related data provided by the voice communications server or location-based and/or shift-based data (e.g., nurse, nurse assistant assignments, etc.) from the voice communications server to override different data from the EHR server, the sync server may analyze all the data to determine confidence values for each. For example, the sync server may evaluate timestamp information of care team assignment data from each source (e.g., EHR server, voice communications server) and provide a higher confidence value to the data with the most recent timestamp. In some embodiments, such confidence operations may be performed in the operations of determination block 532 and/or determination block 538.

FIG. 5C illustrates an embodiment method 550 performed by a sync server to provide up-to-date information of care team assignments based on data from a voice communications server and/or an electronic hospital record (EHR) server. The method 550 is similar to the methods 500, 530 described above reference to FIGS. 5A-5B, except the method 550 may include operations for determining whether update messages may be sent to a server that is sending event-based care team assignment updates. For example, when the EHR server transmits an updated patient-doctor assignment, the sync server may determine that in addition to updating the voice communications server with this updated patient-doctor information, the EHR server should also be updated to include a current nurse assignment for the patient that is not already represented in the data at the EHR server. In this way, more comprehensive synchronization may occur in response to event-based messages.

The operations of blocks 502-508, 516-518 may be similar to the operations of like numbered blocks described above with reference to FIG. 5A, and the operations of blocks 531-542 may be similar to the operations of like numbered blocks described above with reference to FIG. 5B. In response to performing the transmitting operations of block 536, the sync server may determine whether the received event message indicates that there is missing and/or out-of-date data in the EHR server in determination block 552. In particular, the sync server may evaluate the contents of the received event message from the EHR server to identify whether the message reports out-of-date or non-existing location-based and/or shift-based care team assignment data, such as current nurse and/or nurse assistants assigned to a room associated with the received event message. For example, the sync server may evaluate whether the event message from the EHR server includes empty, null, or placeholder data that indicate current or accurate information for such data fields is not known by the EHR server. For example, when the received HL7 message does not include any indication of a current nurse assigned to the patient corresponding to the HL7 message, the sync server may determine the EHR server does not have that data to report. As another example, when the received HL7 message includes information indicating that a room's attending nurse is "Unknown" or "null", the sync server may determine that the nurse care team assignment data field at the EHR server is incomplete.

As another example, when the received HL7 message includes data that indicates the current nurse assistant for the patient's room is "June"; however, the obtained data records indicate the room is currently associated with the nurse assistant "August", the sync server may determine the EHR server has out-of-date information.

In some embodiments, the sync server may compare timestamps or other date information of the received event message to the timestamp or date information of the identified data record to determine whether the EHR server is utilizing out-of-date care team assignment data.

In response to determining that there is missing and/or out-of-date data in the EHR server (i.e., determination block 552="Yes"), the sync server may transmit an update message to the EHR server including the missing and/or out-of-date data from the identified data record in block 554. Such an update message may be similar to the message transmitted with the operations of block 542 as described above, such as an update message sent to an EHR interface engine that relays the data to the EHR server.

In response to performing the transmitting operations of block 542, the sync server may determine whether the received event message indicates that there is missing and/or out-of-date data in the voice communications server in determination block 562. In particular, the sync server may evaluate the contents of the event message from the voice communications server to identify whether the message reports out-of-date or non-existing patient-based care team assignment data, such as the patient's current physician, hospitalist, and/or other information associated with the patient that may be most up-to-date as reported by the EHR server. For example, the sync server may evaluate whether there the event message from the voice communications server includes empty, null, or placeholder data that indicate current or accurate information for such data fields is not known by the voice communications server. For example, when the received subscription notification via the established HTTP connection with the voice communications server does not include any indication of a current general physician assigned to the bed or patient corresponding to the subscription message, the sync server may determine the voice communications server does not have that data to report.

As another example, when the subscription message includes information indicating that a patient's hospitalist is "Unknown" or "null", the sync server may determine that the hospitalist data field at the voice communications server is incomplete. As another example, when the received subscription message includes data that indicates the specialist physician (e.g., cardiologist) for the patient's room is "Dr. B"; however, the obtained data records indicate the room is currently associated with the cardiologist "Dr. T", the sync server may determine the voice communications server has out-of-date information.

In some embodiments, the sync server may compare timestamps or other date information of the received event message to the timestamp or date information of the identified data record to determine whether the voice communications server is utilizing out-of-date care team assignment data.

In response to determining that there is missing and/or out-of-date data in the voice communications server (i.e., determination block 562="Yes"), the sync server may transmit an update message to the voice communications server including the missing and/or out-of-date data from the identified data record in block 564. Such an update message may be similar to the message transmitted with the operations of block 536 as described above, such as an "AddMember" or "removeMember" message transmitted to the voice communications server via an established VAI connection (i.e., a TCP connection and VAI API call).

In response to determining that there is no missing and/or out-of-date data in the voice communications server (i.e., determination block 562="No"), or in response to determining that there is no missing and/or out-of-date data in the EHR server (i.e., determination block 552="No"), or in response to performing the operations of block 554 or 564, the sync server may continue with the operations of optional determination block 516. In response to determining there is missing data in the identified data record (i.e., optional determination block 516="Yes"), the sync server may transmit a message indicating the missing data in optional block 518 and repeat the operations described above by again receiving event messages in block 504. In response to determining there is no missing data in the identified data record (i.e., optional determination block 516="No"), the sync server may repeat the operations described above by again receiving event messages in block 504.

Figure 6:
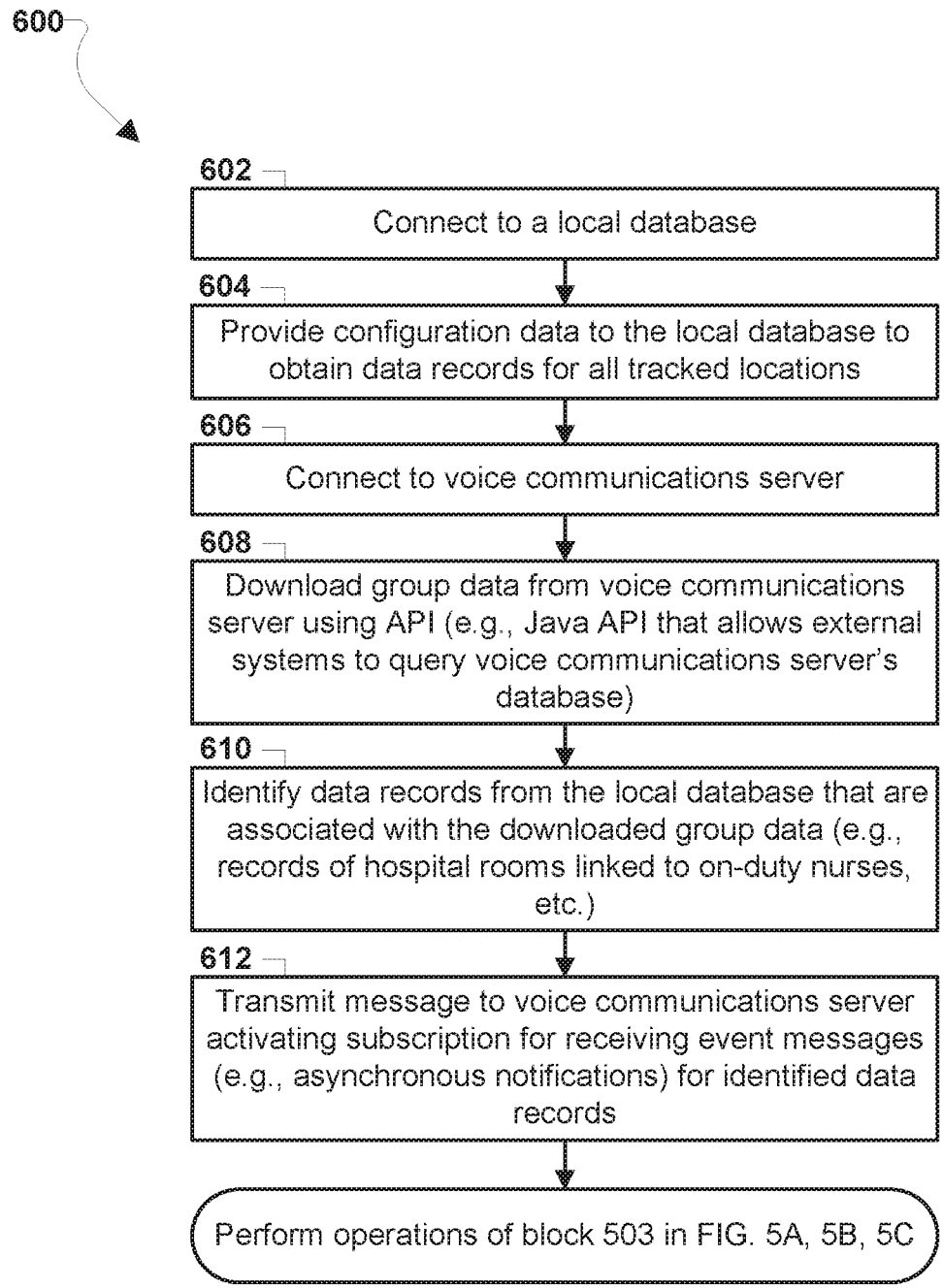
FIG. 6 is a process flow diagram that illustrates an embodiment method performed by a sync server to subscribe to event messages from a voice communications server.

FIG. 6 illustrates an embodiment method 600 that may be performed by a sync server to subscribe to event messages from a voice communications server. The method 600 may be performed during an initialization phase or as a preparatory operation for synchronization operations, such as illustrated above with reference to FIGS. 5A-5C. For example, during an initialization phase, the sync server may perform the method 600 prior to performing synchronization operations using various care team assignment datasets received from an EHR server and the voice communications server.

In block 602, the sync server may connect to a local database, such as a MySQL database connected to or otherwise accessible to the sync server. In block 604, the sync server may provide configuration data to the local database to obtain data records for all tracked locations. For example, the configuration data may be information that causes the database to return data tables that include data records for all rooms, beds, and/or wings of a particular hospital.

In block 606, the sync server may connect to the voice communications server, such as by establishing an HTTP connection. In block 608, the sync server may download group data from the voice communications server using API calls. Such calls may be Java API calls that allow external systems to query the voice communications server's local database to receive data records indicating current care team assignments.

In block 610, the sync server may identify data records from the local database that are associated with the downloaded group data, such as all records of hospital rooms linked to on-duty nurses, etc. In block 612, the sync server may transmit a message to the voice communications server activating a subscription for receiving event messages (e.g., asynchronous notifications) for the identified data records. The sync server may then begin to perform the operations of block 503 as described above with reference to FIG. 5A-5C.

Figure 7A:
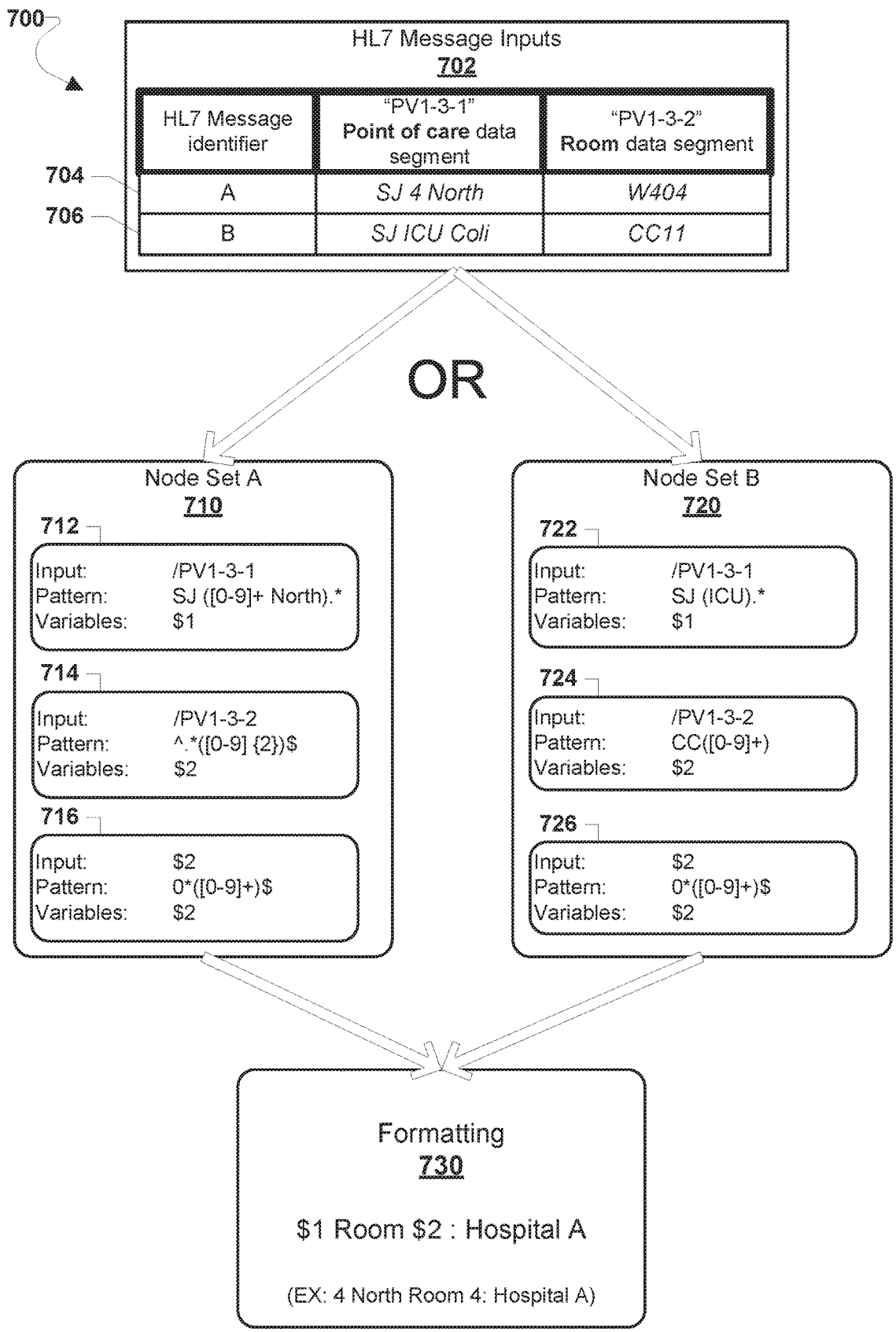
FIG. 7A is a component block diagram of exemplary modules used by a sync server to normalize message data (e.g., HL7 message data) from a server (e.g., an EHR server).
Figure 7B:
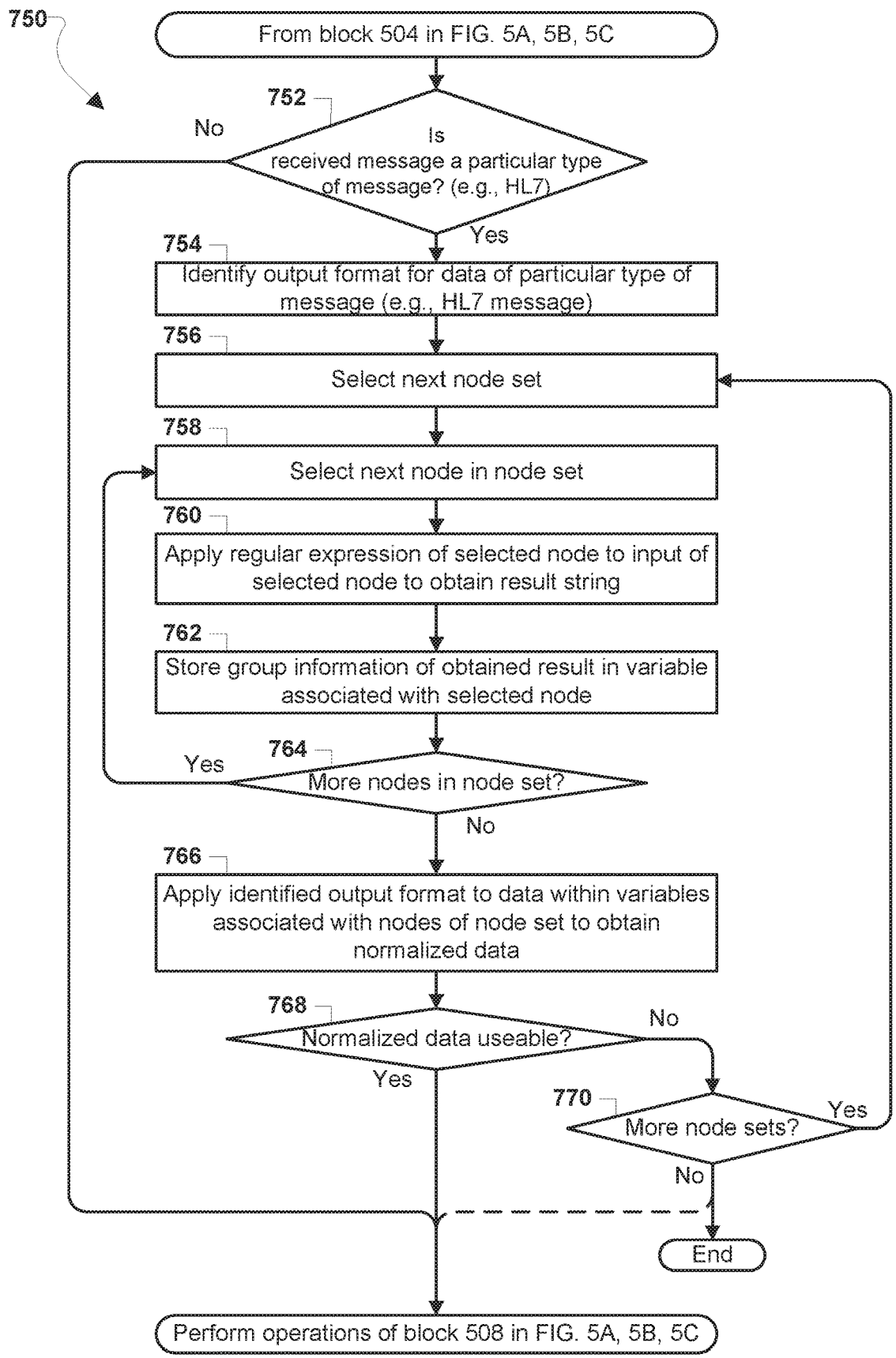
FIG. 7B is a process flow diagram that illustrates an embodiment method performed by a sync server to normalize data from messages (e.g., HL7 messages, etc.) received from another server (e.g., an EHR server, etc).

FIGS. 7A-7C illustrate embodiment normalization functionalities of a sync server. As described above, in some cases, the EHR server may store care team assignment data in a format different than a voice communications server. In order for the sync server to compare data from each server, the data from the EHR server and/or the voice communications server that is received at the sync server may be normalized for processing. For example, the sync server may perform translation or normalizing routines to data received from the EHR server in order to make that received data utilize formatting consistent with or comparable to the formatting of the data from the voice communications server, and vice versa.

In some embodiments, to perform such normalizing, the sync server may utilize normalization operations that include "nodes", such as blocks of code in an XML structure. Each node may be part of a node set and further may be executed by the sync server in order to process input strings from the EHR server and/or the voice communications server. In some embodiments, such nodes may include or utilize an input string related to a location (e.g., "SJ 4 North", "W404", etc.), regular expression(s) for performing pattern matching on the input string, variables that may be used to store input data and/or the results of applying pattern matching (e.g., output variables to place the matched groups from applying the regular expression, etc.), and optional lists of sub-nodes for further analyzing input data.

During embodiment normalization operations, the sync server may evaluate various nodes (e.g., nodes within an XML structure or code) to accumulate pattern matching results within variables. When all nodes and sub nodes of a node set can be traversed (e.g., from top node to leaf node of a node set or tree), the sync server may determine that the input data received from one of the other servers (e.g., from the EHR server, from the voice communications server) can be properly formatted for comparison with other data (e.g., received data originating from the EHR server is comparable to previously received data originating from the voice communications server data, and vice versa).

For the purposes of simplicity, the following descriptions with reference for FIGS. 7A-7C may indicate that normalization operations are applied to data received from the EHR server. However, in some embodiments and/or scenarios, the sync server may also perform normalization operations on data received from the voice communications server in order to generate data with common terms, regardless of the originating server.

FIG. 7A includes a diagram 700 illustrating exemplary modules 702, 710, 720, 730 that may be used by a sync server to normalize HL7 message data from an EHR server. The modules 702, 710, 720, 730 may be or be included within logic, routines, software, circuitry, and/or any other functionality accessible by the processor of the sync server.

The HL7 message inputs module 702 may identify data segments from various HL7 messages 704, 706 received at the sync server. For example, the inputs module 702 may identify that both HL7 messages 704, 706 may include a "PV1-3-1" data segment (i.e., a point of care segment) and a "PV1-3-2" data segment (i.e., a room segment). The inputs module 702 may provide the data segments of each message 704, 706 to the first node set module 710 and/or the second node set module 720.

The first node set module 710 may be configured to process the text of the data segments of the HL7 messages 704, 706 by applying the regular expressions of the nodes 712, 714, 716 and the second node set module 720 may be configured to process the text of the data segments of the HL7 messages 704, 706 by applying the regular expressions of the nodes 722, 724, 726. For example, the first node set module 710 may identify output strings based on matching text of groups (e.g., text between '(' ')') of the regular expressions of the nodes 712-716.

As an illustration of the pattern-matching operations of the first node set module 710, the first node 712 may take the point of care data segment (i.e., "PV1-3-1") from both of the HL7 messages 704, 706 and store in a first variable ($1) a digit (e.g., [0-9]) and the string "North" when the data segments include a digit (e.g., [0-9]) and the string "North" occurring after the text "SJ". The second node 714 may take the room data segment (i.e., "PV1-3-2") from both of the HL7 messages 704, 706 and store in a second variable ($2) two digits (e.g., [0-9]) when the data segments include two digits (e.g., [0-9]) that occur at the end of the room data segment. The third node 716 may take the strings stored in the second variable in response to the operations of the second node 714 and remove any '0' digits that occur at the beginning of the strings, storing any truncated strings back in the second variable ($2).

As an illustration of the pattern-matching operations of the second node set module 720, the first node 722 may take the point of care data segment (i.e., "PV1-3-1") from both of the HL7 messages 704, 706 and store in a first variable ($1) the string "ICU" when the data segments include the string "ICU" after the text "SJ". The second node 724 may take the room data segment (i.e., "PV1-3-2") from both of the HL7 messages 704, 706 and store in a second variable ($2) digits (e.g., [0-9]) that occur after the string "CC". The third node 726 may take the strings stored in the second variable in response to the operations of the second node 724 and remove any '0' digits that occur at the beginning of the strings, storing any truncated strings back in the second variable ($2).

In some embodiments, the inputs module 702 may provide the data segments of each message 704, 706 to the first node set module 710 first and may only provide the data segments of each message 704, 706 to the second node set module 720 in response to determining the first node set module 710 cannot find any useable data based on its pattern matching. For example, in response to determining that no text of the first HL7 message data segments is returned after processing with the first node set module 710, the first HL7 message data segments may be processed with the second node set module 720 to determine whether there are any matches.

The node set modules 710, 720 may provide the data stored in the first and second variables ($1, $2) to a formatting module 730 that may generate a resulting string by inserting the stored data into an output equation. An example of the output equation may be "$1 Room $2: Hospital A", and an example output from this equation may be "4 North Room 4: Hospital A" when the data stored in the first variable is the string "4 North" and the data stored in the second variable is the string "4". Such a normalized output may be used by the sync server in comparisons with data having the same formatted received from the voice communications server.

FIG. 7B illustrates an embodiment method 750 that may be performed by a sync server to normalize data from received messages (e.g., HL7 messages received from an EHR server, messages from voice communications server). For example, EHR data received via HL7 messages (e.g., from an EHR interface engine) may be formatted such that text data indicating location information (e.g., bed number, room number, hospital wing, etc.) is structured the same way as text data indicating location information received from the voice communications server. In some embodiments, the operations of the method 750 may be performed by the sync server in place of the operations of optional block 506 with reference to any of FIGS. 5A-5C.

In determination block 752, the sync server may determine whether the received message is a particular (or predefined/known) type of message (e.g., an HL7 message, a voice communications server message). For example, the sync server may analyze descriptive codes, text, flags, and/or other data associated with incoming messages to determine whether the messages are HL7 messages, etc. In some embodiments, the sync server may recognize incoming messages as HL7 messages or not based on their sender and/or reception port/interface. For example, the sync server may determine that incoming messages from an EHR interface engine are HL7 messages relayed from the EHR server.

In response to determining that the received message is a particular type of message (e.g., an HL7 message, etc.) (i.e., determination block 752="Yes"), the sync server may identify an output format for data of that particular type of message (e.g., HL7 message) in block 754. For example, when the particular message type is associated with HL7 messages, the sync server may identify the formatting used by care team assignment data received from a voice communications server, such as particular spacing, syntax, and string requirements. In some embodiments, the identified output format may correspond to an output equation as illustrated with the formatting module of FIG. 7A.

In block 756, the sync server may select a next node set in normalizing routine. For example, the sync server may select the first node set within an XML structure the first time the normalization operations are performed for the received message. In block 758, the sync server may select a next node in the selected node set, such as by selecting the first node within the selected node set in the XML structure the first iteration of processing the node set.

In block 760, the sync server may apply a regular expression of the selected node to an input of the selected node in order to obtain a result string. In other words, the sync server may perform pattern matching on an input string from the received message, such as text data in a room data segment of a received HL7 message. The input string may be stored in a variable as illustrated above with reference to FIG. 7A. Applying the regular expression may comprise evaluating the input string to detect whether particular subtexts are present in the input string, such as particular numbers of digits or substrings having particular locations (or context) within the entire input string.

In block 762, the sync server may store group information of the obtained result in a variable associated with the selected node. When no matching occurs using the input string and the regular expression, the result may be null or an empty string.

In determination block 764, the sync server may determine whether there are more nodes in the node set to execute, such as sub nodes associated with the selected node. For example, the sync server may evaluate an XML structure to determine whether there are nested nodes defined within the selected node. In response to determining there are additional nodes in the node set to execute (i.e., determination block 764="Yes"), the sync server may continue with the operations in block 756 for selecting the next node.

In response to determining there are no additional nodes in the node set to execute (i.e., determination block 764="No"), the sync server may apply the identified output format to the data within the variables associated with the nodes of node set to obtain normalized data in block 766. For example, the sync server may use the output format to insert text strings stored within the variables into other, predefined text strings (e.g., insert the text string in $1 variable before the predefined text "Room" and the text string in $2 variable after the predefined text "Room", etc.).

In determination block 768, the sync server may determine whether the normalized data is useable for synchronization operations. For example, when the data within the variables was null or empty, the sync server may determine that the normalizing was unsuccessful because no string text was matched using the regular expressions of the nodes of the selected node set.

In response to determining that the normalized data is not useable (i.e., determination block 768="No"), the sync server may determine whether there are more node sets to evaluate in determination block 770.

In response to determining there are more node sets to evaluate (i.e., determination block 770="Yes"), the sync server may continue with the selection operations in block 756. In some embodiments, in response to determine there are no more node sets (i.e., determination block 770="No"), the sync server may end its operations as there may not be any appropriate data to sync with additional operations of the methods described with reference to FIGS. 5A, 5B, 5C.

In response to determining that the received message is not a message of a particular type (e.g., HL7 message, etc.) (i.e., determination block 752="No"), or in response to determining that the normalized data is useable (i.e., determination block 768="Yes"), the sync server may continue with the operations of block 508 as described above with reference to FIG. 5A, 5B, or 5C. In some embodiments, in response to determine there are no more node sets (i.e., determination block 770="No"), the sync server may not end its operations, but instead may continue with the operations of block 508.

In some embodiments, the sync server may utilize an input XML structure to define how to transform data, such as data from the EHR server. An exemplary XML code 799 for use in normalizing operations is shown in FIG. 7C. In some embodiments, when run within a normalizing routine, software, etc., such code 799 may return a 'true' or 'false' value indicating whether normalization was successfully performed on input strings from the EHR server.

Figure 8:
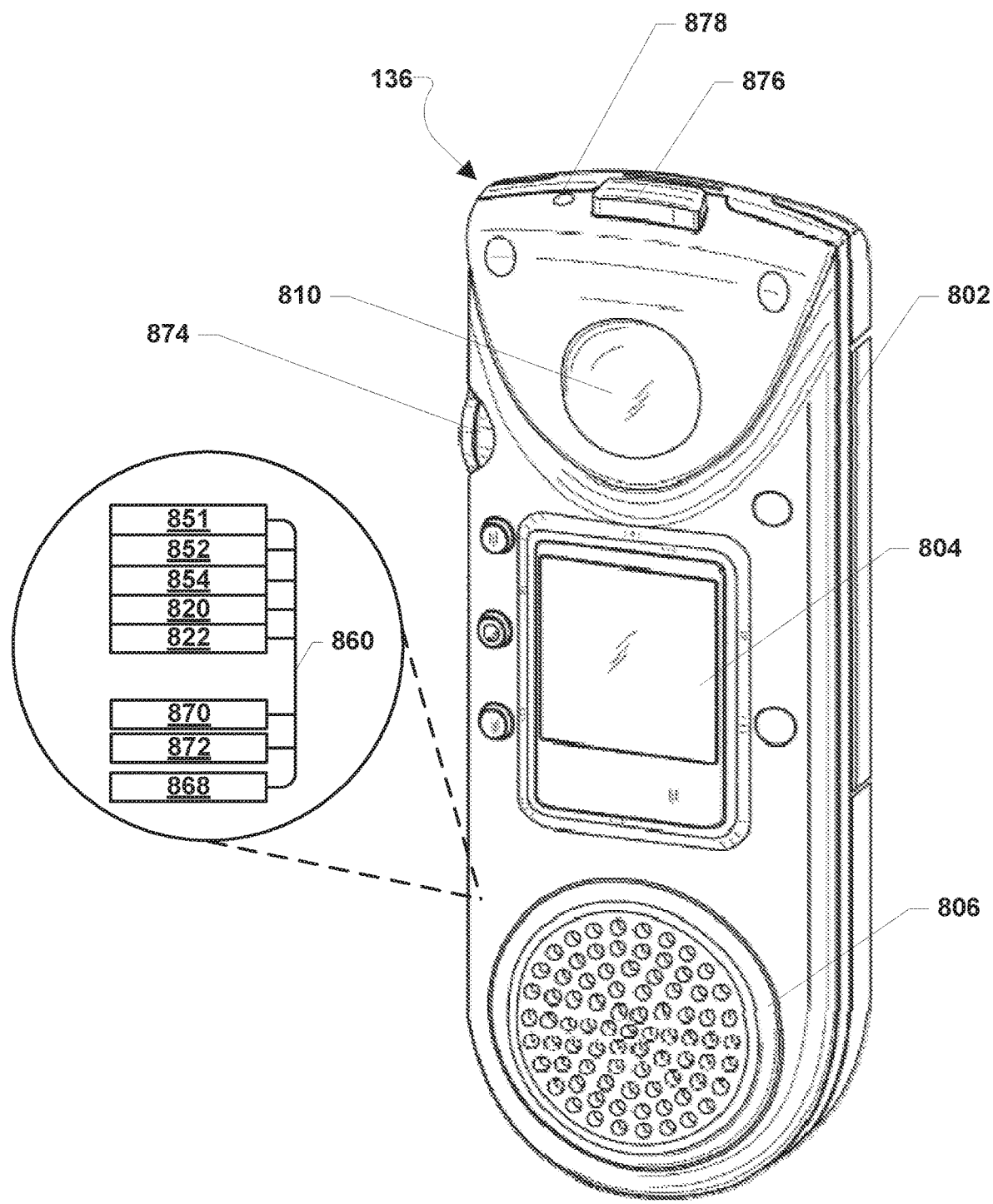
FIG. 8 is a component block diagram of a voice communications badge device suitable for use in some embodiments.

FIG. 8 illustrates an exemplary voice communications badge device 136 suitable for use in various embodiments. The voice communications badge device 136 may include a housing 802 that holds various components. In particular, the voice communications badge device 136 may include a microphone 810, a speaker 806, and a display device 804, such as a liquid crystal display (LCD). Various data may be displayed on the display device 804, such as data for reviewing text messages and pages received by the voice communications badge device 136 and/or data to permit the user to control the operation of the voice communications badge device 136 and its configuration using a control menu or to announce the origin of an incoming call. The microphone 810 and speaker 806 may also be used for voice communications with other voice communications badge device 136 users or third parties. In some embodiments, the voice communications badge device 136 may further include an amplifier that amplifies the signals provided to/from the microphone and speaker.

The voice communications badge device 136 may further include an input device 874 that permits the user to control the operation of the voice communications badge device 136 and its configuration. In some embodiments, the input device 874 may be a jog switch that may be a spring-loaded compound-action switch that supports three momentary actions. In particular, the switch may be pressed inwards as an ordinary push button. In some embodiments, the input device 874 may also be rotated in either direction and/or may be a touch button location in particular location (e.g., on the front of the voice communications badge device 136) that may be pushed or touched to activate the same functions and operations being activated by the jog switch. The voice communications badge device 136 may also include an on/off switch 876 and a status indicator 878 (e.g., an LED that may be capable of displaying one or more different colors to signal the operational status of the voice communications badge device 136, etc.). In some embodiments, the voice communications badge device 136 may optionally include a headset jack that enables the user to plug in an external microphone/speaker headset, such as an ear bud.

Internally, the voice communications badge device 136 may include a central processing unit (CPU) or processor 851 that controls the operation of the voice communications badge device 136 and each of its components. For example, the processor 851 may control the operations of the microphone 810 and the speaker 806 so that the user of the voice communications badge device 136 may exchange voice commands/responses with remote devices (e.g., a voice communications server, etc.). The voice communications badge device 136 may further include a non-volatile memory device 852 so that data stored in the voice communications badge device 136 (such as settings and messages) are not lost when the voice communications badge device 136 is powered down. For example, the non-volatile memory device 852 may be a storage unit or other memory device configured to store at least a factory-assigned a unique physical media access control (MAC) address or unique wireless device address. The voice communications badge device 136 may also include a wireless transceiver 820 (e.g., an appropriate strength 802.11 transceiver, etc.) and an antenna 822 that may be used for wireless communications with various access points or with other devices (e.g., other voice communications badge devices 136, etc.).

The voice communications badge device 136 may include a renewable energy source 868, such as a removable, rechargeable battery that may include protection and charge management circuitry to prevent over charging. For example, the energy source 868 may be a replaceable, rechargeable lithium polymer or lithium ion battery that attaches to the back of the voice communications badge device 136. The voice communications badge device 136 may further include a pager receiver 854 and an internal antenna that operates to receive text messages/pages within the coverage of any global paging service network. In some embodiments, the antennae 822 may be built into an exterior clip of the voice communications badge device 136 or may reside completely within the housing 802 of voice communications badge device 136. The voice communications badge device 136 may further comprise a digital signal processor (DSP) 870 and an audio codec 872 for processing incoming speech from the microphone 810 and for generating the voice signals generated by the speaker 806. For example, the DSP 870 and audio codec 872 may be capable of compressing digital voice data to reduce the amount of digital data used to communicate the voice commands to the server. The various components 851-854, 820, 822, 870, 872, 868 may be connected via a bus 860 or other similar linkage or connectivity.

Exemplary descriptions of various voice communications badge devices suitable for use in various embodiments may also be found in commonly-held patent applications, including U.S. Pat. No. 6,892,083 entitled "Voice-Controlled Wireless Communications System and Method," U.S. Pat. No. 8,098,806 entitled "Non-User-Specific Wireless Communication System and Method," and U.S. Design Pat. D679,673, the content of all of which are incorporated herein.

Various forms of computing devices, including personal computers, mobile computing devices (e.g., smartphones, etc.), servers, laptop computers, etc., may be used to implement the various embodiments. Such computing devices may typically include, at least, the components illustrated in FIG. 9 which illustrates an example server computing device. Such a server computing device 110 may typically include a processor 901 coupled to volatile memory 902 and a large capacity nonvolatile memory, such as a disk drive 903. The server computing device 110 may also include a floppy disc drive, compact disc (CD) or DVD disc drive 906 coupled to the processor 901. The server computing device 110 may also include network access ports 904 (or interfaces) coupled to the processor 901 for establishing data connections with a network 905, such as the Internet and/or a local area network coupled to other system computers and servers.

The various processors described herein may be any programmable microprocessor, microcomputer or multiple processor chip or chips that can be configured by software instructions (applications) to perform a variety of functions, including the functions of the various embodiments described herein. In the various devices, multiple processors may be provided, such as one processor dedicated to wireless communication functions and one processor dedicated to running other applications. Typically, software applications may be stored in internal memory before they are accessed and loaded into the processors. The processors may include internal memory sufficient to store the application software instructions. In many devices the internal memory may be a volatile or nonvolatile memory, such as flash memory, or a mixture of both. For the purposes of this description, a general reference to memory refers to memory accessible by the processors including internal memory or removable memory plugged into the various devices and memory within the processors.

The foregoing method descriptions and the process flow diagrams are provided merely as illustrative examples and are not intended to require or imply that the operations of the various embodiments must be performed in the order presented. Accordingly, the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more exemplary embodiments, the functions described may be implemented in hardware, software, firmware, or any combination thereof. If implemented in software, the functions may be stored on or transmitted over as one or more instructions or code on a non-transitory processor-readable, computer-readable, or server-readable medium or a non-transitory processor-readable storage medium. The operations of a method or algorithm disclosed herein may be embodied in a processor-executable software module or processor-executable software instructions which may reside on a non-transitory computer-readable storage medium, a non-transitory server-readable storage medium, and/or a non-transitory processor-readable storage medium. In various embodiments, such instructions may be stored processor-executable instructions or stored processor-executable software instructions. Tangible, non-transitory computer-readable storage media may be any available media that may be accessed by a computer. By way of example, and not limitation, such non-transitory computer-readable media may comprise RAM, ROM, EEPROM, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray Disc® where disks usually reproduce data magnetically, while discs reproduce data optically with lasers. Combinations of the above should also be included within the scope of non-transitory computer-readable media. Additionally, the operations of a method or algorithm may reside as one or any combination or set of codes and/or instructions on a tangible, non-transitory processor-readable storage medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method of updating hospital personnel assignment data records, comprising:

receiving, by a first server, a first message including information corresponding to a hospital personnel assignment for a predetermined location within a hospital;

determining, by the first server, whether a hospital personnel assignment data record corresponding to the predetermined location within the hospital reflects a current hospital personnel assignment for the predetermined location within the hospital based on whether the first message is received from a second server or a third server; and updating, by the first server, the hospital personnel assignment data record to include the information corresponding to the hospital personnel assignment for the predetermined location within the hospital included in the first message in response to determining that the hospital personnel assignment data record does not reflect the current hospital personnel assignment for the predetermined location, wherein the second server is a different type of server from the first server and the third server, wherein the third server is a different type of server from the first server and the second server, and wherein the second server is an electronic health record (EHR) server and the third server is a voice communication server.

2. The method of claim 1, wherein the information corresponding to the hospital personnel assignment for the predetermined location within the hospital included in the first message comprises location information associated with the hospital and one or more of a hospital personnel role identifier, a unique hospital personnel identifier, hospital personnel shift information, a unique patient identifier, and a patient status identifier.

3. The method of claim 1, wherein the first message indicates a change in the hospital personnel assignment for the predetermined location within the hospital.

4. The method of claim 1, further comprising:
obtaining, by the first server, the hospital personnel assignment data record based on the predetermined location within the hospital in response to receiving the first message,
wherein the hospital personnel assignment data record has a plurality of data fields, and
wherein the plurality of data fields includes a first data field associated with the predetermined location, a second data field associated with information assumed to be accurate when provided by the second server, and a third data field associated with information assumed to be accurate when provided by the third server.

5. The method of claim 4, wherein determining whether the hospital personnel assignment data record corresponding to the predetermined location within the hospital reflects the current hospital personnel assignment for the predetermined location within the hospital comprises:
comparing, by the first server, the information corresponding to the hospital personnel assignment for the predetermined location within the hospital included in the first message to the second data field in response to determining that the first message is received from the third server;
determining, by the first server, that the hospital personnel assignment data record does not reflect the current hospital personnel assignment for the predetermined location within the hospital in response to determining that the second data field is empty or the information within the second data field does not match the information corresponding to the hospital personnel assignment for the predetermined location within the hospital included in the first message; and
determining, by the first server, that the hospital personnel assignment data record reflects the current hospital personnel assignment for the predetermined location within the hospital in response to determining that information within the second data field includes the information corresponding to the hospital personnel assignment for the predetermined location within the hospital included in the first message.

6. The method of claim 4, wherein determining whether the hospital personnel assignment data record corresponding to the predetermined location within the hospital reflects the current hospital personnel assignment for the predetermined location within the hospital comprises:
comparing, by the first server, the information corresponding to the hospital personnel assignment for the predetermined location within the hospital included in the first message to the third data field in response to determining that the first message is received from the second server;
determining, by the first server, that the hospital personnel assignment data record does not reflect the current hospital personnel assignment for the predetermined location within the hospital in response to determining that the third data field is empty or the information within the third data field does not match the information corresponding to the hospital personnel assignment for the predetermined location within the hospital included in the first message; and
determining, by the first server, that the hospital personnel assignment data record reflects the current hospital personnel assignment for the predetermined location within the hospital in response to determining that information within the third data field includes the information corresponding to the hospital personnel assignment for the predetermined location within the hospital included in the first message.

7. The method of claim 1, further comprising:
transmitting, by the first server, a second message to the second server in response to determining that the first message is received from the third server and the hospital personnel assignment data record corresponding to the predetermined location within the hospital does not reflect the current hospital personnel assignment for the predetermined location within the hospital; and
transmitting, by the first server, a third message to the third server in response to determining that the first message is received from the second server and the hospital personnel assignment data record corresponding to the predetermined location within the hospital does not reflect the current hospital personnel assignment for the predetermined location within the hospital.

8. A first server, comprising a processor configured with processor-executable instructions to perform operations comprising:
receiving a first message including information corresponding to a hospital personnel assignment for a predetermined location within a hospital;
determining whether a hospital personnel assignment data record corresponding to the predetermined location within the hospital reflects a current hospital personnel assignment for the predetermined location within the hospital based on whether the first message is received from a second server or a third server; and
updating the hospital personnel assignment data record to include the information corresponding to the hospital personnel assignment for the predetermined location within the hospital included in the first message in response to determining that the hospital personnel assignment data record does not reflect the current hospital personnel assignment for the predetermined location,
wherein the second server is a different type of server from the first server and the third server,
wherein the third server is a different type of server from the first server and the second server, and
wherein the second server is an electronic health record (EHR) server and the third server is a voice communication server.

9. The first server of claim 8, wherein the information corresponding to the hospital personnel assignment for the predetermined location within the hospital included in the first message comprises location information associated with the hospital and one or more of a hospital personnel role identifier, a unique hospital personnel identifier, hospital personnel shift information, a unique patient identifier, and a patient status identifier.

10. The first server of claim 8, wherein the first message indicates a change in the hospital personnel assignment for the predetermined location within the hospital.

11. The first server of claim 8, wherein the processor is configured with processor-executable instructions to perform further operations comprising:
obtaining the hospital personnel assignment data record based on the predetermined location within the hospital in response to receiving the first message,
wherein the hospital personnel assignment data record has a plurality of data fields, and wherein the plurality of data fields includes a first data field associated with the predetermined location, a second data field associated with information assumed to be accurate when provided by the second server, and a third data field associated with information assumed to be accurate when provided by the third server.

12. The first server of claim 11, wherein determining whether the hospital personnel assignment data record corresponding to the predetermined location within the hospital reflects the current hospital personnel assignment for the predetermined location within the hospital comprises:
   comparing the information corresponding to the hospital personnel assignment for the predetermined location within the hospital included in the first message to the second data field in response to determining that the first message is received from the third server;
   determining that the hospital personnel assignment data record does not reflect the current hospital personnel assignment for the predetermined location within the hospital in response to determining that the second data field is empty or the information within the second data field does not match the information corresponding to the hospital personnel assignment for the predetermined location within the hospital included in the first message; and
   determining that the hospital personnel assignment data record reflects the current hospital personnel assignment for the predetermined location within the hospital in response to determining that information within the second data field includes the information corresponding to the hospital personnel assignment for the predetermined location within the hospital included in the first message.

13. The first server of claim 11, wherein determining whether the hospital personnel assignment data record corresponding to the predetermined location within the hospital reflects the current hospital personnel assignment for the predetermined location within the hospital comprises:
   comparing the information corresponding to the hospital personnel assignment for the predetermined location within the hospital included in the first message to the third data field in response to determining that the first message is received from the second server;
   determining that the hospital personnel assignment data record does not reflect the current hospital personnel assignment for the predetermined location within the hospital in response to determining that the third data field is empty or the information within the third data field does not match the information corresponding to the hospital personnel assignment for the predetermined location within the hospital included in the first message; and
   determining that the hospital personnel assignment data record reflects the current hospital personnel assignment for the predetermined location within the hospital in response to determining that information within the third data field includes the information corresponding to the hospital personnel assignment for the predetermined location within the hospital included in the first message.

14. The first server of claim 8, wherein the processor is configured with processor-executable instructions to perform further operations comprising:
   transmitting a second message to the second server in response to determining that the first message is received from the third server and the hospital personnel assignment data record corresponding to the predetermined location within the hospital does not reflect the current hospital personnel assignment for the predetermined location within the hospital; and
   transmitting a third message to the third server in response to determining that the first message is received from the second server and the hospital personnel assignment data record corresponding to the predetermined location within the hospital does not reflect the current hospital personnel assignment for the predetermined location within the hospital.

15. A non-transitory processor-readable storage medium having stored thereon processor-executable instructions configured to cause a processor of a first server to perform operations comprising:
   receiving a first message including information corresponding to a hospital personnel assignment for a predetermined location within a hospital;
   determining whether a hospital personnel assignment data record corresponding to the predetermined location within the hospital reflects a current hospital personnel assignment for the predetermined location within the hospital based on whether the first message is received from a second server or a third server; and
   updating the hospital personnel assignment data record to include the information corresponding to the hospital personnel assignment for the predetermined location within the hospital included in the first message in response to determining that the hospital personnel assignment data record does not reflect the current hospital personnel assignment for the predetermined location,
   wherein the second server is a different type of server from the first server and the third server,
   wherein the third server is a different type of server from the first server and the second server, and
   wherein the second server is an electronic health record (EHR) server and the third server is a voice communication server.

16. The non-transitory processor-readable storage medium of claim 15, wherein the information corresponding to the hospital personnel assignment for the predetermined location within the hospital included in the first message comprises location information associated with the hospital and one or more of a hospital personnel role identifier, a unique hospital personnel identifier, hospital personnel shift information, a unique patient identifier, and a patient status identifier.

17. The non-transitory processor-readable storage medium of claim 15, wherein the first message indicates a change in the hospital personnel assignment for the predetermined location within the hospital.

18. The non-transitory processor-readable storage medium of claim 15, wherein the stored processor-executable instructions are configured to cause the processor of the first server to perform further operations comprising:
   obtaining the hospital personnel assignment data record based on the predetermined location within the hospital in response to receiving the first message,
   wherein the hospital personnel assignment data record has a plurality of data fields, and
   wherein the plurality of data fields includes a first data field associated with the predetermined location, a second data field associated with information assumed to be accurate when provided by the second server, and a third data field associated with information assumed to be accurate when provided by the third server.

19. The non-transitory processor-readable storage medium of claim 18, wherein the stored processor-executable instructions are configured to cause the processor of the first server to perform operations such that determining whether the hospital personnel assignment data record corresponding to the predetermined location within the hospital reflects the current hospital personnel assignment for the predetermined location within the hospital comprises:

comparing the information corresponding to the hospital personnel assignment for the predetermined location within the hospital included in the first message to the second data field in response to determining that the first message is received from the third server;

determining that the hospital personnel assignment data record does not reflect the current hospital personnel assignment for the predetermined location within the hospital in response to determining that the second data field is empty or the information within the second data field does not match the information corresponding to the hospital personnel assignment for the predetermined location within the hospital included in the first message; and determining that the hospital personnel assignment data record reflects the current hospital personnel assignment for the predetermined location within the hospital in response to determining that information within the second data field includes the information corresponding to the hospital personnel assignment for the predetermined location within the hospital included in the first message.

20. The non-transitory processor-readable storage medium of claim 18, wherein the stored processor-executable instructions are configured to cause the processor of the first server to perform operations such that determining whether the hospital personnel assignment data record corresponding to the predetermined location within the hospital reflects the current hospital personnel assignment for the predetermined location within the hospital comprises:

comparing the information corresponding to the hospital personnel assignment for the predetermined location within the hospital included in the first message to the third data field in response to determining that the first message is received from the second server;

determining that the hospital personnel assignment data record does not reflect the current hospital personnel assignment for the predetermined location within the hospital in response to determining that the third data field is empty or the information within the third data field does not match the information corresponding to the hospital personnel assignment for the predetermined location within the hospital included in the first message; and determining that the hospital personnel assignment data record reflects the current hospital personnel assignment for the predetermined location within the hospital in response to determining that information within the third data field includes the information corresponding to the hospital personnel assignment for the predetermined location within the hospital included in the first message.

21. The non-transitory processor-readable storage medium of claim 15, wherein the stored processor-executable instructions are configured to cause the processor of the first server to perform further operations comprising:

transmitting a second message to the second server in response to determining that the first message is received from the third server and the hospital personnel assignment data record corresponding to the predetermined location within the hospital does not reflect the current hospital personnel assignment for the predetermined location within the hospital; and transmitting a third message to the third server in response to determining that the first message is received from the second server and the hospital personnel assignment data record corresponding to the predetermined location within the hospital does not reflect the current hospital personnel assignment for the predetermined location within the hospital.

\* \* \* \* \*